United States Patent [19]
Ueda et al.

[11] Patent Number: 4,725,601
[45] Date of Patent: Feb. 16, 1988

[54] CERTAIN IMIDAZO[1,2-a]PYRIDINES USEFUL IN THE TREATMENT OF ULCERS

[75] Inventors: Ikuo Ueda, Uenohigashi; Youichi Shiokawa, Ibaraki; Kazuhiko Take, Uriwarinishi; Hiromichi Itani, Ikeda, all of Japan

[73] Assignee: Fujisawa Pharmaceutical Co., Ltd., Osaka, Japan

[21] Appl. No.: 865,331

[22] Filed: May 21, 1986

[30] Foreign Application Priority Data

Jun. 4, 1985 [GB] United Kingdom ................ 8514080
Dec. 16, 1985 [GB] United Kingdom ................ 8530878

[51] Int. Cl.$^4$ ...................... A61K 31/44; C07D 471/04
[52] U.S. Cl. .................................... 514/300; 546/121; 514/249; 544/350

[58] Field of Search .......................... 546/121; 514/300

[56] References Cited

U.S. PATENT DOCUMENTS 4,450,164  5/1984  Bristol et al. ........................ 546/121
4,507,294  3/1985  Bristol et al. ........................ 514/249

FOREIGN PATENT DOCUMENTS 0033094  8/1981  European Pat. Off. .

Primary Examiner—Alan L. Rotman
Assistant Examiner—Bernard I. Dentz
Attorney, Agent, or Firm—Oblon, Fisher, Spivak, McClelland & Maier

[57] ABSTRACT

Certain imidazo[1,2-a]heterocyclic compounds useful in the treatment of ulcers are provided.

11 Claims, No Drawings

CERTAIN IMIDAZO[1,2-a]PYRIDINES USEFUL IN THE TREATMENT OF ULCERS

The present invention relates to novel imidazoheterocyclic compounds and pharmaceutically acceptable salt thereof. More particularly, it relates to novel imidazoheterocyclic compounds and pharmaceutically acceptable salts thereof which have antiulcerative activity, to processes for preparation thereof, to a pharmaceutical composition comprising the same, and to a method of using the same therapeutically in the treatment of ulcer in human or animals.

Accordingly, one object of the present invention is to provide novel imidazoheterocyclic compounds and pharmaceutically acceptable salt thereof, which are useful as an antiulcerative agent.

Another object of the present invention is to provide processes for preparation of said imidazoheterocyclic compounds and salts thereof.

A further object of the present invention is to provide a pharmaceutical composition comprising, as an active ingredient, said imidazoheterocyclic compound or its pharmaceutically acceptable salt.

Still further object of the present invention is to provide a method of using said imidazoheterocyclic compound or its pharmaceutically acceptable salt in the treatment of ulcer in human or animals.

The imidazoheterocyclic compounds of the present invention are novel and can be represented by the formula (I):

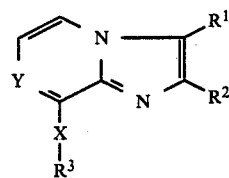

(I)

wherein
- $R^1$ is lower alkenyl, lower alkynyl, lower alkadienyl, lower alkenyloxy(lower)alkyl, lower alkynyloxy(lower)alkyl, carboxy(lower)alkynyloxy(lower)alkyl or protected carboxy(lower)alkynyloxy(lower)alkyl;
- $R^2$ is hydrogen, lower alkyl or aryl,
- $R^3$ is ar(lower)alkyl which may have one or more suitable substituent(s), ar(lower)alkenyl, condensed bicyclic hydrocarbon group, lower alkyl having cyclo(lower)alkyl or lower alkyl,
- X is O or NH, and
- Y is CH or N.

According to the present invention, the object compounds (I) can be prepared by the following processes.

Process 1

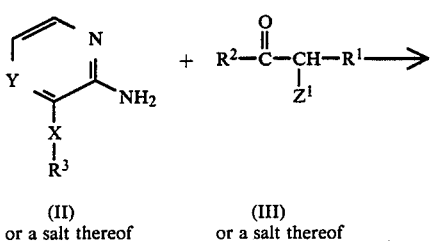

(II) or a salt thereof    (III) or a salt thereof

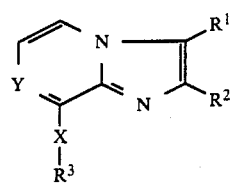

(I) or a salt thereof

Process 2

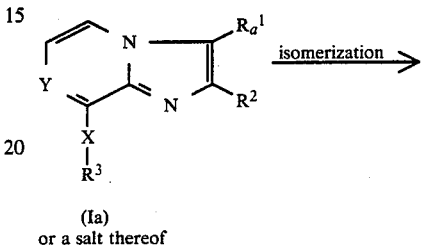

(Ia) or a salt thereof

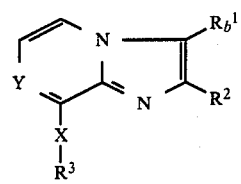

(Ib) or a salt thereof

Process 3

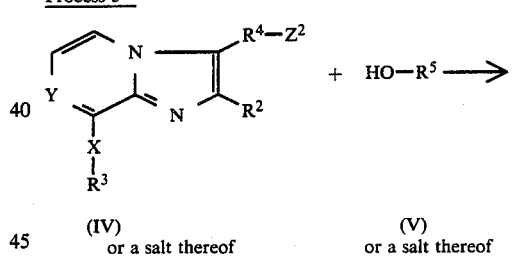

(IV) or a salt thereof    (V) or a salt thereof

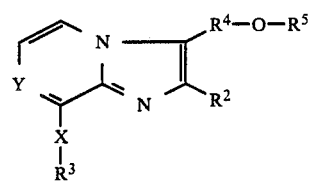

(Ic) or a salt thereof

Process 4

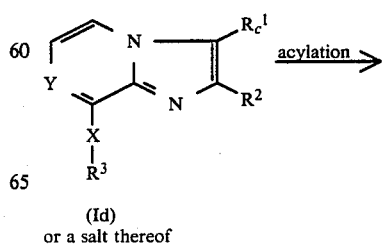

(Id) or a salt thereof

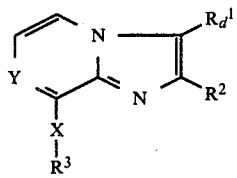

(Ie)

or a salt thereof wherein
$R^1$, $R^2$, $R^3$, X and Y are each as defined above,
$R_a^1$ is lower alkynyl,
$R_b^1$ is cumulated lower alkadienyl,
$R_c^1$ is (ω-lower alkynyloxy)(lower)alkyl,
$R_d^1$ is (ω-carboxy-ω-lower alkynyloxy)(lower)alkyl or (ω-protected carboxy-ω-lower alkynyloxy)(lower)alkyl,
$R^4$ is lower alkylene,
$R^5$ is lower alkenyl, lower alkynyl, carboxy(lower)alkynyl or protected carboxy(lower)alkynyl,
$Z^1$ is an acid residue, and
$Z^2$ is a leaving group.

As to the starting compounds (II), (III) and (IV), some of them are novel and can be prepared by the procedures disclosed in the Preparations as mentioned later.

Especially, some of said novel starting compound (II) can be represented by the following general formula:

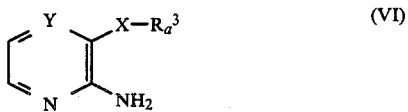

(VI)

wherein
$R_a^3$ is lower alkyl having cyclo(lower)alkyl or ar(lower)alkyl which may have one or more substituent(s),
X is O or NH, and
Y is CH or N,
provided that when X is O and Y is CH, then $R_a^3$ is lower alkyl having cyclo(lower)alkyl.

Suitable pharmaceutically acceptable salts of the object compounds (I) are conventional non-toxic salts and include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an organic acid addition salt (e.g. acetate, maleate, tartrate, methanesulfonate, benzenesulfonate, formate, toluenesulfonate, etc.), an inorganic acid addition salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "lower alkyl" may be the ones having 1 to 6 carbon atom(s) and may include methyl, ethyl, propyl, isopropyl, n-butyl, t-butyl, pentyl, hexyl, and the like, in which the preferred one may be $C_1$–$C_4$alkyl and the more preferred one may be methyl and ethyl.

Suitable "lower alkenyl" may be the ones having 2 to 6 carbon atoms and may include vinyl, allyl, isopropenyl, 1(or 2 or 3)-butenyl, 1(or 2 or 3 or 4)-pentenyl, 1(or 2 or 3 or 4 or 5)-hexenyl, and the like, in which the preferred one may be $C_2$–$C_4$alkenyl and the more preferred one may be allyl.

Suitable "lower alkynyl" may be the ones having 2 to 6 carbon atoms and may include ethynyl, 1(or 2)-propynyl, 1(or 2 or 3)-butynyl, 1-methyl-2-propynyl, 1(or 2 or 3 or 4)-pentynyl, 1(or 2 or 3 or 4 or 5)-hexynyl, and the like, in which the preferred one may be $C_2$–$C_4$alkynyl and the more preferred one may be 2-propynyl.

Suitable "lower alkadienyl" may be the ones having 3 to 6 carbon atoms and may include 1,2-propadienyl, 1,2-butadienyl, 1,3-butadienyl, 2,3-pentadienyl, 1,4-pentadienyl, 1,2-hexadienyl, 1,3-hexadienyl, 1,4-hexadienyl, and the like, in which the preferred one may be $C_3$–$C_5$ alkadienyl and the more preferred one may be 1,2-propadienyl.

"Cumulated lower alkadienyl" means the above-defined "lower alkadienyl" group in which two double bonds are adjacent to each other through one carbon atom, and suitable examples of such "cumulated lower alkadienyl" may include 1,2-propadienyl, 1,2-butadienyl, 2,3-pentadienyl, 1,2-hexadienyl, and the like, in which the preferred one may be cumulated $C_3$–$C_5$alkadienyl and the more preferred one may be 1,2-propadienyl.

In the term "lower alkenyloxy(lower)alkyl", suitable "lower alkenyl" moiety and "(lower)alkyl" moiety can be referred to the ones as mentioned above, respectively, and suitable examples of such "lower alkenyloxy(lower)alkyl" may include vinyloxymethyl, allyloxymethyl, 1-allyloxyethyl, 1-allyloxypropyl, 3-allyloxybutyl, 3-(2-butenyloxy)butyl, 5-(3-pentenyloxy)pentyl, 1-(2-hexenyloxy)hexyl, and the like, in which the preferred one may be ($C_2$–$C_4$)alkenyloxy($C_1$–$C_4$)alkyl and the more preferred one may be allyloxymethyl.

In the term "lower alkynyloxy(lower)alkyl", suitable "lower alkynyl" moiety and "(lower)alkyl" moiety can be referred to the ones as mentioned above, respectively, and suitable examples of such "lower alkynyloxy(lower)alkyl" may include ethynyloxymethyl, 2-propynyloxymethyl, 2-(2-propynyloxy)ethyl, 1-(2-butynyloxy)propyl, 1-(3-butynyloxy)propyl, 2-(3-butynyloxy)butyl, 3-(3-butynyloxy)butyl, 4-(1-pentynyloxy)pentyl, 4-(4-pentynyloxy)pentyl, 5-(5-hexynyloxy)hexyl, 6-(5-hexynyloxy)hexyl, and the like, in which the preferred one may be ($C_2$–$C_4$)alkynyloxy($C_1$–$C_4$)alkyl and the more preferred one may be 2-propynyloxymethyl.

"Carboxy(lower)alkynyloxy(lower)alkyl" means the above-defined lower alkynyloxy(lower)alkyl group which is substituted with carboxy, and suitable examples of such "carboxy(lower)alkynyloxy(lower)alkyl" may include carboxyethynyloxymethyl, 3-carboxy-2-propynyloxymethyl, 1-carboxy-2-2-propynyloxymethyl, 2-(3-carboxy-2-propynyloxy)ethyl, 1-(1-carboxy-2-butynyloxy)propyl, 1-(4-carboxy-3-butynyloxy)propyl, 2-(4-carboxy-3-butynyloxy)butyl, 3-(4-carboxy-3-butynyloxy)butyl, 4-(3-carboxy-1-pentynyloxy)pentyl, 4-(5-carboxy-4-pentynyloxy)pentyl, 5-(1-carboxy-5-hexynyloxy)hexyl, 6-(6-carboxy-5-hexynyloxy)hexyl, and the like, in which the preferred one may be carboxy($C_2$–$C_4$)alkynyloxy($C_1$–$C_4$)alkyl and the more preferred one may be 3-carboxy-2-propynyloxymethyl.

"Protected carboxy(lower)alkynyloxy(lower)alkyl" means the above-defined lower alkynyloxy(lower)alkyl group which is substituted with protected carboxy, and suitable "protected carboxy" may be an esterified carboxy or the like, and concrete examples of the ester moiety in said esterified carboxy may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester bis(methoxyphenyl)methyl ester, 3,4-dimethoxybenzyl ester, 4-hydroxy-3,5-di-tertbutylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable examples of the "protected carboxy(lower)alkynyloxy(lower)alkyl" thus defined may be (lower)alkoxycarbonyl(lower)alkynyloxy(lower)alkyl such as methoxycarbonylethynyloxymethyl, 3-ethoxycarbonyl-2-propynyloxymethyl, 1-ethoxycarbonyl-2-propynyloxymethyl, 2-(3-ethoxycarbonyl-2-propynyloxy)ethyl, 1-(1-propoxycarbonyl-2-butynyloxy)propyl, 1-(4-ethoxycarbonyl-3-butynyloxy)propyl, 2-(4-butoxycarbonyl-3-butynyloxy)butyl, 3-(4-tert-butoxycarbonyl-3-butynyloxy)butyl, 4-(3-pentyloxycarbonyl-1-pentynyloxy)pentyl, 4-(5-ethoxycarbonyl-4-pentynyloxy)pentyl, 5-(1-hexyloxycarbonyl-5-hexynyloxy)hexyl, 6-(6-hexyloxycarbonyl-5-hexynyloxy)hexyl, and the like, in which the preferred one may be ($C_1$–$C_4$)alkoxycarbonyl($C_2$–$C_4$)alkynyloxy($C_1$–$C_4$)alkyl and the more preferred one may be 3-ethoxycarbonyl-2-propynyloxymethyl.

Suitable "carboxy(lower)alkynyl" may be the same as that in the terms of "carboxy(lower)alkynyloxy(lower)alkyl" and may include carboxyethynyl, 3-carboxy-2-propynyl, 1-carboxy-2-propynyl, 1-carboxy-2-butynyl, 4-carboxy-3-butynyl, 3-carboxy-1-pentynyl, 1-carboxy-5-hexynyl, 6-carboxy-5-hexynyl, and the like, in which the preferred one may be carboxy($C_2$–$C_4$)alkynyl and the more preferred one may be 3-carboxy-2-propynyl.

Suitable "protected carboxy(lower)alkynyl" may be the same as that in the terms of "protected carboxy(lower)alkynyloxy(lower)alkyl" and may include lower alkoxycarbonyl(lower)alkynyl such as methoxycarbonylethynyl, 3-ethoxycarbonyl-2-propynyl, 1-ethoxycarbonyl-2-propynyl, 1-propoxycarbonyl-2-butynyl, 4-ethoxycarbonyl-3-butynyl, 4-butoxycarbonyl-3-butynyl, 4-tert-butoxycarbonyl-3-butynyl, 3-pentyloxycarbonyl-1-pentynyl, 1-hexyloxycarbonyl-5-hexynyl, 6-hexyloxycarbonyl-5-hexynyl, and the like, in which the preferred one may be ($C_1$–$C_4$)alkoxycarbonyl($C_2$–$C_4$)alkynyl and the more preferred one may be 3-ethoxycarbonyl-2-propynyl.

"(ω-Lower alkynyloxy)(lower)alkyl" means the above-defined lower alkynyloxy(lower)alkyl group, in which the triple bond always exists on the terminal carbon atom of the lower alkynyl moiety, and suitble examples of such "(ω-lower alkynyloxy)(lower)alkyl" may include ethynyloxymethyl, 2-propynyloxymethyl, 2-(2-propynyloxy)ethyl, 1-(3-butynyloxy)propyl, 2-(3-butynyloxy)butyl, 4-(4-pentynyloxy)pentyl, 6-(5-hexynyloxy)hexyl, and the like, in which the preferred one may be [ω-($C_2$–$C_4$)alkynyloxy]($C_1$–$C_4$)alkyl and the more preferred one may be 2-propynyloxymethyl.

"(ω-Carboxy-ω-lower alkynyloxy)(lower)alkyl" means the above-defined ω-lower alkynyloxy(lower)alkyl group which is substituted with carboxy on the terminal carbon atom of the lower alkynyl moiety, and suitable examples of such "(ω-carboxy-ω-lower alkynyloxy)(lower)alkyl" may include carboxyethynyloxymethyl, 3-carboxy-2-propynyloxymethyl, 2-(3-carboxy-2-propynyloxy)ethyl, 1-(4-carboxy-3-butynyloxy)propyl, 2-(4-carboxy-3-butynyloxy)butyl, 4-(5-carboxy-4-pentynyloxy)pentyl, 6-(6-carboxy-5-hexynyloxy)hexyl and the like, in which the preferred one may be [ω-carboxy-ω-($C_2$–$C_4$)alkynyloxy]($C_1$–$C_4$)alkyl and the more preferred one may be 3-carboxy-2-propynyloxymethyl.

"(ω-Protected carboxy-ω-lower alkynyloxy)(lower)alkyl" means the above-defined ω-lower alkynyloxy(lower)alkyl group which is substituted with protected carboxy as mentioned above on the terminal carbon atom of the lower alkynyl moiety, and suitable examples of such "(ω-protected carboxy-ω-lower alkynyloxy)(lower)alkyl" may be (ω-lower alkoxycarbonyl-ω-lower alkynyloxy)(lower)alkyl such as methoxycarbonylethynyloxymethyl, 3-ethoxycarbonyl-2-propynyloxymethyl, 2-(3-ethoxycarbonyl-2-propynyloxy)ethyl, 1-(4-propoxycarbonyl-3-butynyloxy)propyl, 3-(4-tert-butoxycarbonyl-3-butynyloxy)butyl, 4-(5-pentyloxycarbonyl-4-pentynyloxy)pentyl, 5-(6-hexyloxycarbonyl-5-hexynyloxy)hexyl, and the like, in which the preferred one may be [ω-($C_1$–$C_4$)alkoxycarbonyl-ω-($C_2$–$C_4$)alkynyloxy]($C_1$–$C_4$)alkyl and the more preferred one may be 3-ethoxycarbonyl-2-propynyloxymethyl.

Suitable "aryl" may include phenyl, tolyl, xylyl, 1-naphthyl, 2-naphthyl, 1-anthryl, 2-anthryl, and the like, in which the preferred one may be phenyl.

Suitable "ar(lower)alkyl" may include mono-(or di- or tri-)phenyl(lower)alkyl such as benzyl, 1-phenylethyl, 2-phenylethyl, 2-phenylpropyl, 3-phenylbutyl, 1-methyl-2-phenylpropyl, 5-phenylpentyl, 4-phenylhexyl, benzhydryl, 2,3-diphenylpropyl, trityl, 1,2,3-triphenylbutyl, etc.; naphthyl(lower)alkyl such as 1-naphthylmethyl, 2-naphthylmethyl, 1-(2-naphthyl)ethyl, 3-(1-naphthyl)propyl, 2-(2-naphthyl)butyl, 5-(1-naphthyl)pentyl, 4-(2-naphthyl)hexyl, etc.; and the like, in which the preferred one may be phenyl($C_1$–$C_4$)alkyl and naphthyl ($C_1$–$C_4$)alkyl, and the more preferred one may be benzyl, 1-phenylethyl, 2-phenylethyl, 1-naphthylmethyl and 2-naphthylmethyl.

Said "ar(lower)alkyl" may have one or more (preferably 1 to 3) suitable substituent(s) selected from a group consisting of lower alkyl (e.g. methyl, ethyl, propyl, isopropyl, butyl, pentyl, hexyl, etc.) and halogen (e.g. fluoro, chloro, bromo, iodo), and the preferred examples of said substituted ar(lower)alkyl may be mono or di halophenyl(lower)alkyl (e.g. 2-chlorobenzyl, 3-chlorobenzyl, 4-chlorobenzyl, 2-bromobenzyl, 4-bromobenzyl, 2-fluorobenzyl, 4-fluorobenzyl, 4-iodobenzyl, 2-chlorophenethyl, 2,3-dichlorobenzyl, 2,4-dichlorobenzyl, 3,4-dichlorobenzyl, 2,6-dichlorobenzyl, 2-chloro-4-fluorobenzyl, etc.), mono or di(lower)alkylphenyl(lower)alkyl (e.g. 2-methylbenzyl, 3-methylbenzyl, 4-methylbenzyl, 2-methylphenethyl, 2-ethylbenzyl, 2-propylbenzyl, 2-isopropylbenzyl, 3-butylbenzyl, 4-pentylbenzyl, 2-hexylbenzyl, 2,3-dimethylbenzyl, 2,6-dimethylbenzyl, 2,4-diethylbenzyl, 2-methyl-4-propylbenzyl, etc.), and the more preferred one may be mono or dihalophenyl($C_1$-$C_4$)alkyl and mono or di($C_1$-$C_4$)alkyl phenyl($C_1$-$C_4$)alkyl, and the most preferred one may be 2-chlorobenzyl, 3-chlorobenzyl, 2-bromobenzyl, 2-fluorobenzyl, 2,4-dichlorobenzyl, 3,4-dichlorobenzyl, 2,6-dichlorobenzyl, 2-methylbenzyl, 2-ethylbenzyl, 2-isopropylbenzyl and 2,6-dimethylbenzyl.

Suitable "ar(lower)alkenyl" may include mono(or di or tri)-phenyl(lower)alkenyl such as styryl, cinnamyl, phenylbutenyl (e.g. 4-phenyl-2-butenyl, 2-phenyl-3-butenyl, etc.), phenylpentenyl (e.g. 1-phenyl-1-pentenyl, etc.), phenylhexenyl (e.g. 4-phenyl-2-hexenyl, etc.), 2,3-diphenyl-1-butenyl, 2,3,4-triphenyl-4-pentenyl, and the like, in which the preferred one may be phenyl($C_2$-$C_4$)alkenyl and the more preferred one may be cinnamyl.

Suitable "condensed bicyclic hydrocarbon group" may include naphthyl, 1,4-dihydronaphthyl, indenyl, benzene-condensed cyclo(lower)alkyl (e.g. 1,2,3,4-tetrahydronaphthyl, 2,3-dihydroindenyl, etc.), perhydroindenyl and the like, in which the preferred one may be benzene-condensed cyclo($C_5$-$C_6$)alkyl and the more preferred one may be 1,2,3,4-tetrahydronaphthyl.

Suitable "lower alkyl having cyclo(lower)alkyl" may include cyclopropylmethyl, cyclobutylmethyl, cyclopentylethyl, cyclohexylmethyl, cyclohexylethyl, cyclohexylpropyl, cyclohexylbutyl, cyclohexylpentyl, cyclohexylhexyl, and the like, in which the preferred one may be cyclo($C_5$-$C_6$)alkyl($C_1$-$C_4$)alkyl and the more preferred one may be cyclohexylmethyl.

Suitable "lower alkylene" may include methylene, ethylene, trimethylene, propylene, tetramethylene, pentamethylene, hexamethylene and the like, in which the preferred one may be $C_1$-$C_4$ alkylene and the more preferred one may be methylene.

Suitable "an acid residue" may include halogen (e.g. fluorine, chlorine, bromine, iodine), acyloxy (e.g. acetoxy, tosyloxy, mesyloxy, etc.), and the like.

Suitable "a leaving group" may include an acid residue as mentioned above, a group of the formula:

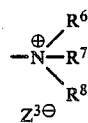

wherein
$R^6$, $R^7$ and $R^8$ are each lower alkyl as mentioned above, and
$Z^3$ is an acid residue as mentioned above, and the like.

The processes for preparing the object compounds of the present invention are explained in detail in the following.

Process 1

The object compound (I) or a salt thereof can be prepared by reacting the compound (II) or a salt thereof with the compound (III) or a salt thereof.

Suitable salts of the compound (II) can be referred to the acid addition salt as exemplified for the compound (I) and those of the compound (III) can be referred to the salt with a base for the same.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at ambient temperature or under warming or heating.

Process 2

The object compound (Ib) or a salt thereof can be prepared by subjecting the compound (Ia) or a salt thereof to isomerization reaction of lower alkynyl into cumulated lower alkadienyl.

Suitable salts of the compounds (Ia) and (Ib) can be referred to the acid addition salts as exemplified for the compound (I).

This reaction is usually carried out in the presence of a base such as an alkali metal hydroxide (e.g. sodium hydroxide, potassium hydroxide, etc.), an alkali metal carbonate (e.g. sodium carbonate, potassium carbonate, etc.), or the like.

This reaction is usually carried out in a solvent such as alcohol (e.g. methanol, ethanol, etc.), N,N-dimethylformamide or any other solvent which does not adversely affect the reaction.

The reaction temperature is not critical, and the reaction can be carried out at ambient temperature or under warming or heating.

Process 3

The object compound (Ic) or a salt thereof can be prepared by reacting the compound (IV) or a salt thereof with the compound (V) or a salt thereof.

Suitable salts of the compound (IV) can be referred to the acid addition salts as exemplified for the object compound (I).

Suitable salts of the compound (Ic) can be referred to the ones as exemplified for the object compound (I).

Suitable salts of the compound (V) are salts with a base such as an alkali metal salt (e.g. sodium salt, potassium salt, lithium salt, etc.), or the like.

This reaction is usually carried out in the presence of a base such as alkali metal hydride (e.g. sodium hydride, potassium hydride, lithium hydride, etc.), alkali metal alkoxide (e.g. potassium t-butoxide, etc.), an alkali metal (e.g. sodium, potassium, lithium, etc.) or the like.

This reaction is usually carried out in a solvent such as alcohol [e.g. methanol, ethanol, etc.], dimethyl sulfoxide, benzene, N,N-dimethylformamide, tetrahydrofuran, diethyl ether or any other solvent which does not adversely affect the reaction.

In case that the compound (V) or a salt thereof to be used is liquid, it can also be used as a solvent.

The reaction temperature is not critical, and the reaction can be carried out under cooling, at ambient temperature or under warming or heating.

Process 4

The object compound (Ie) or a salt thereof can be prepared by subjecting the compound (Id) or a salt thereof to acylation reaction.

Suitable salts of the compound (Id) can be referred to the acid addition salts as exemplified for the compound (I).

Suitable salts of the compound (Ie) can be referred to the ones as exemplified for the compound (I).

The acylation reaction of this process can be carried out by reacting the compound (Id) or a salt thereof with a conventional agent which can introduce a carboxy or a protected carboxy group into a terminal carbon atom of ω-lower alkynyl such as carbon dioxide gas, dry ice, lower alkoxy(halo)formate (e.g. ethyl chloroformate, etc.), di(lower)alkyl carbonate (e.g. dimethyl carbonate, diethyl carbonate, etc.), di(lower)alkyl oxalate (e.g. diethyl oxalate, etc.), tri(lower)alkyl phosphonoacetate (e.g. triethyl phosphonoacetate, etc.).

This reaction is usually carried out in the presence of a base such as metalated lower alkyl (e.g. methyl lithium, n-butyl lithium, etc.), metalated aryl (e.g. phenyl lithium, etc.), alkali metal hydride (e.g. sodium hydride, potassium hydride, etc.) or the like.

This reaction is usually carried out in a solvent such as diethyl ether, tetrahydrofuran, N,N-dimethylformamide, n-hexane or any other solvent which does not adversely affect the reaction.

The reaction temperature is not critical, and the reaction can be carried out under cooling or at ambient temperature.

The object compounds (I) and their pharmaceutically acceptable salts of the present invention are novel and exhibit high antiulcerative activity.

In order to illustrate the usefulness of the object compounds (I), the pharmacological data of some representative compounds of the object compounds (I) are shown in the following.

(A) Inhibition on ethanol ulcer

Test Method:

Five male Spraque-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm) in the medicated group was compared with that in the control group.

Test compounds (1) 8-(2-Methylbenzyloxy)-3-(2-propynyloxymethyl)-2-methylimidazo[1,2-a]pyridine
(2) 8-(2-Chlorobenzyloxy)-3-(2-propynyloxymethyl)-2-methylimidazo[1,2-a]pyridine
(3) 8-(2-Methylbenzyloxy)-3-(2-propynyl)-2-methylimidazo[1,2-a]pyridine Test Results (A) Inhibition % at the dose of 32 mg/kg:

| Test Compound | Inhibition % |
| --- | --- |
| (1) | 94.4 |
| (2) | 98.2 |
| (3) | 91.8 |

(B) The $ED_{50}$ value of the Test Compound (1): 1.1 mg/kg (B) Inhibition on stress ulcer Test Method:

Five Sprague-Dawley rats weighing about 200 g were used per group. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area ($mm^2$) in the medicated animals was compared with that in the control animals.

Test Compounds (1) 8-(2-Methylbenzyloxy)-3-(2-propynyloxymethyl)-2-methylimidazo[1,2-a]pyridine
(2) 8-(2-Chlorobenzyloxy)-3-(2-propynyloxymethyl)-2-methylimidazo[1,2-a]pyridine
(3) 8-(2-Methylbenzyloxy)-3-(2-propynyl)-2-methylimidazo[1,2-a]pyridine Test Results (A) Inhibition % at the dose of 32 mg/kg:

| Test Compound | Inhibition % |
| --- | --- |
| (1) | 100 |
| (2) | 100 |
| (3) | 100 |

(B) The $ED_{50}$ value of the Test Compound (1): 0.15 mg/kg

As being apparent from the above test results, the object compound (I) of the present invention are useful as an antiulcerative agent.

For therapeutic purpose, the compounds according to the present invention can be used in a form of pharmaceutical preparation containing said compound as an active ingredient, in admixture with a pharmaceutically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 5 mg, 10 mg, 50 mg, 100 mg, 250 mg, 500 mg, and 1000 mg of the compounds according to the present invention may be effective for treating ulcer. In general, amounts between 1 mg/body and about 2,000 mg/body or even more may be administered per day.

The following preparations and examples are given for the purpose of illustrating the present invention.

Preparation 1

A solution of 5-hexen-2-one (3.92 g) in N,N-dimethylformamide (4 ml) was added to mixture of cupric chloride dihydrate (13.636 g) and lithium chloride (3.392 g) in N,N-dimethylformamide (20 ml) at 80° C. After being stirred at 80°–90° C. for 1 hour, the mixture was poured into cold water and extracted with ethyl acetate. The extract was washed with water, dried over magnesium sulfate and evaporated in vacuo to give a crude oil of 3-chloro-5-hexen-2-one (3.01 g) which was used for the next step without purification.

Preparation 2

Tosyl chloride (3.81 g) was added to a solution of 3-hydroxy-5-hexyn-2-one (2.24 g) and triethylamine (2.424 g) in methylene chloride (20 ml) under ice-cooling. After being stirred for 2.5 hours, the mixture was washed with water, dried over magnesium sulfate and evaporated in vacuo. The oily residue was purified by column chromatography on silica gel (60 g) using methylene chloride as an eluent to give an oil of 3-tosyloxy-5-hexyn-2-one (2.94 g).

IR (film/NaCl): 3280, 1720, 1590, 1360 (broad) cm$^{-1}$
NMR (CCl$_4$, δ): 1.79 (1H, t, J=2 Hz), 2.25 (3H, s), 2.43 (3H, s), 2.3–2.6 (2H, m), 4.66 (1H, t, J=5 Hz), 7.31 (2H, d, J=8 Hz), 7.78 (2H, d, J=8 Hz).

Preparation 3

Mesyl chloride (1.73 ml) was added dropwise to a solution of 3-hydroxy-2-methoxy-1-hexen-5-yne (2 g) and triethylamine (3.32 ml) in methylene chloride (20 ml) under ice-cooling over a period of 10 minutes. After being stirred for 48 hours at room temperature the mixture was washed successively with water, aqueous sodium bicarbonate solution, and brine, dried over magnesium sulfate, and evaporated in vacuo to give 3-mesyloxy-2-methoxy-1-hexen-5-yne (3.45 g).

IR (film/NaCl): 3280, 2110 cm$^{-1}$
NMR (CCl$_4$, δ): 1.96 (1H, t, J=3 Hz), 2.63–2.80 (2H, m), 2.95 (3H, s), 3.62 (3H, s), 4.22 (1H, d, J=3 Hz), 4.40 (1H, d, J=3 Hz), 4.93 (1H, t, J=6 Hz).

Preparation 4

To a solution of 3-mesyloxy-2-methoxy-1-hexen-5-yne (0.5 g) in acetone (1.5 ml) was added 20% sulfuric acid (1.5 ml) under ice-cooling and the mixture was stirred for 1.5 hours under the same conditions and then for 1.5 hours at room temperature. Acetone was evaporated in vacuo and the residue was extracted with methylene chloride. The extract was washed successively with water, aqueous sodium bicarbonate solution, and brine, dried over magnesium sulfate, and evaporated in vacuo to give 3-mesyloxy-5-hexyn-2-one (0.41 g).

IR (film/NaCl): 3290, 2120, 1720 cm$^{-1}$
NMR (CCl$_4$, δ): 2.03 (1H, t, J=3 Hz), 2.31 (3H, s) 2.70–2.86 (2H, m), 3.11 (3H, s), 4.92 (1H, t, J=6 Hz).

Preparation 5

To a mixture of 2-amino-3-hydroxypyridine (7 g) and Adogen 464 (Trademark: prepared by Aldrich Chemical Co.) (0.4 g) in 40% aqueous sodium hydroxide (32 ml) and methylene chloride (32 ml) was added 2-methylbenzyl chloride (8.42 ml) at ambient temperature. After being stirred for 24 hours, the organic layer was separated and the aqueous layer was extracted with methylene chloride. The combined extracts were washed with saturated sodium chloride aqueous solution, dried over magnesium sulfate, and evaporated in vacuo. The crystalline residue was recrystallized from ethyl acetate to give 2-amino-3-(2-methylbenzyloxy)-pyridine (7.56 g).

mp: 100° to 101° C.
IR (Nujol): 3450, 3275, 3125, 1625 cm$^{-1}$
NMR (CDCl$_3$, δ): 2.40 (3H, s), 4.68 (2H, s), 5.05 (2H, s), 6.43–6.73 (1H, m), 6.98 (1H, dd, J=2 Hz and 8 Hz), 7.10–7.46 (4H, m), 7.66 (1H, dd, J=2 Hz and 5 Hz).

Preparation 6

The following compounds were prepared according to a similar manner to that of Preparation 5.

(1) 2-Amino-3-(2-ethylbenzyloxy)pyridine
mp: 93° to 95° C. (recrystallized from a mixture of ethyl acetate and n-hexane)
IR (Nujol): 3475, 3275, 3130, 1620 cm$^{-1}$
NMR (CDCl$_3$, δ): 1.27 (3H, t, J=8 Hz), 2.73 (2H, q, J=8 Hz), 4.68 (2H, broad s), 5.07 (2H, s), 6.43–6.73 (1H, m), 6.99 (1H, d, J=7 Hz), 7.12–7.50 (4H, m), 7.66 (1H, dd, J=2 Hz and 5 Hz).

(2) 2-Amino-3-(2-isopropylbenzyloxy)pyridine
mp: 106° to 107° C. (recrystallized from a mixture of ethyl acetate and n-hexane)
IR (Nujol): 3450, 3275, 3120, 1620 cm$^{-1}$
NMR (CDCl$_3$, δ): 1.25 (6H, d, J=6 Hz), 2.50–3.45 (1H, m), 4.63 (2H, broad s), 5.05 (2H, s), 6.43–6.75 (1H, m), 7.02 (1H, d, J=8 Hz), 7.15–7.48 (4H, m), 7.66 (1H, dd, J=2 Hz and 5 Hz).

(3) 2-Amino-3-(2-chlorobenzyloxy)pyridine
mp: 100° to 101° C. (recrystallized from methylene chloride)
IR (Nujol): 3465, 3275, 3120, 1620 cm$^{-1}$
NMR (CDCl$_3$, δ): 4.73 (2H, broad s), 5.15 (2H, s), 6.40–6.70 (1H, m), 6.92 (1H, dd, J=2 Hz and 8 Hz), 7.10–7.50 (4H, m), 7.65 (1H, dd, J=2 Hz and 5 Hz).

(4) 2-Amino-3-(3-chlorobenzyloxy)pyridine
mp: 87.5° to 89° C. (recrystallized from a mixture of methylene chloride and n-hexane)
IR (Nujol): 3480, 3275, 3100, 1622 cm$^{-1}$
NMR (CDCl$_3$, δ): 4.88 (2H, broad s), 4.97 (2H, s), 6.40–6.63 (1H, m), 6.89 (1H, d, J=8 Hz), 7.27 (3H, s), 7.38 (1H, s), 7.65 (1H, dd, J=2 Hz and 5 Hz).

(5) 2-Amino-3-(2-bromobenzyloxy)pyridine
mp: 107° to 108° C. (recrystallized from ethyl acetate)
IR (Nujol): 3440, 3270, 3125, 1617 cm$^{-1}$
NMR (CDCl$_3$, δ): 4.80 (2H, broad s), 5.11 (2H, s), 6.46–6.70 (1H, m), 6.94 (1H, dd, J=1.5 Hz and 7.5 Hz), 7.06–7.76 (5H, m).

(6) 2-Amino-3-(2,6-dimethylbenzyloxy)pyridine
mp: 151° to 155° C. (recrystallized from a mixture of ethyl acetate and n-hexane)
IR (Nujol): 3470, 3280, 3145, 1620 cm$^{-1}$
NMR (CDCl$_3$, δ): 2.47 (6H, s), 4.68 (2H, broad s), 5.01 (2H, s), 6.48–6.71 (1H, m), 6.97–7.28 (4H, m), 7.68 (1H, dd, J=2 Hz and 5 Hz).

(7) 2-Amino-3-(2,6-dichlorobenzyloxy)pyridine
mp: 146° to 148° C. (recrystallized from methanol)
IR (Nujol): 3455, 3270, 3125, 1620 cm$^{-1}$
NMR (CDCl$_3$, δ): 4.70 (2H, broad s), 5.28 (2H, s), 6.45–6.73 (1H, m), 7.02–7.53 (4H, m), 7.67 (1H, dd, J=2 Hz and 5 Hz).

(8) 2-Amino-3-(2-naphthylmethoxy)pyridine
mp: 138° to 139° C.

NMR (CDCl$_3$, δ): 4.73 (2H, broad s), 5.22 (2H, s), 6.40–6.70 (1H, m), 6.96 (1H, dd, J=2 Hz and 7 Hz), 7.30–8.0 (8H, m).

(9) 2-Amino-3-(1-naphthylmethoxy)pyridine
  mp: 146° to 148° C. (recrystallized from ethyl acetate)
  NMR (CDCl$_3$, δ): 4.72 (2H, broad s), 5.38 (2H, s), 6.36 (1H, dd, J=5 Hz and 8 Hz), 7.02 (1H, d, J=8 Hz), 7.30–8.13 (8H, m).

(10) 2-Amino-3-cinnamyloxypyridine (trans isomer)
  mp: 127° to 129° C. (recrystallized from a mixture of ethyl acetate and n-hexane)
  IR (Nujol): 3475, 3275, 3120, 1620 cm$^{-1}$
  NMR (CDCl$_3$, δ): 4.66 (2H, d, J=5 Hz), 4.79 (2H, broad s), 6.14–7.02 (4H, m), 7.20–7.48 (5H, m), 7.66 (1H, dd, J=2 Hz and 5 Hz).

(11) 2-Amino-3-(1,2,3,4-tetrahydro-1-naphthyloxy)pyridine
  mp: 106.5° to 107° C. (recrystallized from a mixture of ethyl acetate and n-hexane)
  IR (Nujol): 3475, 3300, 3140, 1626 cm$^{-1}$
  NMR (CDCl$_3$, δ): 1.60–2.36 (4H, m), 2.63–3.06 (2H, m), 4.63 (2H, broad s), 5.20–5.46 (2H, m), 6.46–6.75 (1H, m), 6.98–7.50 (5H, m), 7.65 (1H, dd, J=1 Hz and 5 Hz).

(12) 2-Amino-3-cyclohexylmethoxypyridine
  mp: 110° to 112° C.
  NMR (CDCl$_3$, δ): 0.63–2.10 (11H, m), 3.78 (2H, d, J=6 Hz), 4.69 (2H, broad s), 6.43–6.73 (1H, m), 6.90 (1H, dd, J=2 Hz and 8 Hz), 7.64 (1H, dd, J=2 Hz and 5 Hz).

Preparation 7

Molecular Sieves (16 g) was added to a solution of 2,3-diaminopyridine (8 g), 2-methylbenzaldehyde (8.81 g), and acetic acid (4.2 ml) in methanol (160 ml) and the mixture was stirred for 96 hours at room temperature. Sodium cyanoborohydride (4.61 g) was added portionwise to the mixture with stirring under ice-cooling over a period of 20 minutes. After being stirred for 3 hours, the mixture was made alkaline with aqueous sodium bicarbonate solution and filtered by suction. The filtrate was evaporated in vacuo, and to the residue was added water and then extracted with methylene chloride. The extract was washed with brine, dried over magnesium sulfate, and evaporated in vacuo. The crystalline residue was recrystallized from a mixture of ethyl acetate and n-hexane to give 2-amino-3-(2-methylbenzylamino)pyridine (5.38 g).
mp: 135° to 140° C.
NMR (CDCl$_3$, δ): 2.36 (3H, s), 3.20–3.63 (1H, broad s), 4.20 (2H, broad d, J=4 Hz), 4.40–5.20 (2H, broad s), 6.50–6.93 (2H, m), 7.0–7.63 (5H, m).

Preparation 8

2-Amino-3-(2-chlorobenzylamino)pyridine was obtained according to a similar manner to that of Preparation 7.
mp: 144° to 147° C.
NMR (CDCl$_3$, δ): 3.60–4.60 (3H, m), 4.36 (2H, d, J=6 Hz), 6.43–6.83 (2H, m), 6.96–7.86 (5H, m).

Preparation 9

To a solution of 2-methylbenzyl alcohol (0.985 g) in N,N-dimethylformamide (10 ml) was added 62.8% sodium hydride (0.308 g) under a nitrogen atmosphere and then stirred for 30 minutes. 2-Amino-3-chloropyrazine (0.87 g) was added to the solution and the mixture was heated at 65° C. for 2 hours and poured onto crushed ice. The resulting precipitates were collected by filtration, washed with n-hexane, and dried in a desiccator to give 2-amino-3-(2-methylbenzyloxy)pyrazine (0.6 g).
mp: 70° to 72° C.
NMR (CDCl$_3$, δ): 2.37 (3H, s), 4.40–5.00 (2H, broad s), 5.34 (2H, s), 7.00–7.45 (4H, m), 7.35 (1H, d, J=3 Hz), 7.48 (1H, d, J=3 Hz).

Preparation 10

A mixture of 2-amino-3-chloropyrazine (4.3 g), 2-methylbenzylamine (4.6 g), potassium carbonate (5.5 g), and potassium iodide (0.4 g) in N,N-dimethylformamide (43 ml) was refluxed for 24 hours under a nitrogen atmosphere and allowed to stand at room temperature. The mixture was poured into water and extracted with ethyl acetate. The extract was washed with water, dried over magnesium sulfate, and evaporated in vacuo. The residue was purified by column chromatography on silica gel (110 g) with a mixture of chloroform and methanol (100:3) as an eluent to give 2-amino-3-(2-methylbenzylamino)pyrazine (1.4 g).
NMR (CDCl$_3$, δ): 2.33 (3H, s), 3.80–4.50 (3H, broad s), 4.50 (2H, d, J=5 Hz), 6.95–7.35 (4H, m), 7.30 (1H, d, J=3 Hz), 7.50 (1H, d, J=3 Hz).

Preparation 11

A 60% dispersion of sodium hydride in mineral oil (1.87 g) was added portionwise to a suspension of 8-hydroxy-2-methylimidazo[1,2-a]pyridine (6.3 g) in dimethyl sulfoxide (63 ml) at room temperature over a period of 15 minutes. After being stirred for 30 minutes, 2-chlorobenzyl chloride (7.54 g) was added in one portion to the mixture and then the resultant mixture was stirred for 24 hours at room temperature. The mixture was poured into water and the resulting precipitate was collected by filtration. The crude product was purified by column chromatography on silica gel (30 g) with methylene chloride as an eluent to afford a solid, which was recrystallized from a mixture of diethyl ether and n-hexane to give 8-(2-chlorobenzyloxy)-2-methylimidazo[1,2-a]pyridine (7.75 g).
mp: 97° to 98° C.
IR (Nujol): 1535, 1280, 1260, 1100 cm$^{-1}$
NMR (CDCl$_3$, δ): 2.46 (3H, s), 5.41 (2H, s), 6.26–6.73 (2H, m), 7.05–7.50 (4H, m), 7.52–7.83 (2H, m).

Preparation 12

The following compounds were obtained according to a similar manner to that of Preparation 11.
(1) 8-(2-Methylbenzyloxy)-2-methylimidazo[1,2-a]pyridine
  mp: 101° to 103° C. (recrystallized from a mixture of ethyl acetate and n-hexane)
  IR (Nujol): 1530, 1485, 1275, 1260, 1095 cm$^{-1}$
  (NMR (CDCl$_3$, δ): 2.36 (3H, s), 2.43 (3H, s), 5.23 (2H, s), 6.28–6.63 (2H, m), 7.0–7.53 (5H, m), 7.59 (1H, dd, J=1.5 Hz and 6 Hz).
(2) 8-(1-Phenylethoxy)-2-methylimidazo[1,2-a]pyridine
  NMR (CDCl$_3$, δ): 1.80 (3H, d, J=7 Hz), 2.52 (3H, s), 5.50 (1H, q, J=7 Hz), 6.06–6.56 (2H, m), 6.93–7.66 (7H, m).
(3) 8-(3-Chlorobenzyloxy)-2-methylimidazo[1,2-a]pyridine
  mp: 108° to 110° C. (recrystallized from a mixture of ethyl acetate and n-hexane)
  IR (Nujol): 1590, 1530, 1490, 1275, 1260, 1160, 1100 cm$^{-1}$ NMR (CDCl$_3$, δ): 2.46 (3H, s), 5.26 (2H, s), 6.25–6.75 (2H, m), 7.15–7.45 (4H, m), 7.50 (1H, s), 7.63 (1H, dd, J=2 Hz and 6 Hz).
(4) 8-(2-Bromobenzyloxy)-2-methylimidazo[1,2-a]pyridine
mp: 113° to 114° C. (recrystallized from diethyl ether)
NMR (CDCl$_3$, δ): 2.54 (3H, s), 5.43 (2H, s), 6.29–6.76 (2H, m), 7.10–7.80 (6H, m).
(5) 8-(2,6-Dichlorobenzyloxy)-2-methylimidazo[1,2-a]pyridine
mp: 157° to 160° C.
NMR (CDCl$_3$, δ): 2.43 (3H, s), 5.45 (2H, s), 6.46–6.76 (2H, m), 7.13–7.46 (4H, m), 7.56–7.76 (1H, m)
(6) 8-(2,4-Dichlorobenzyloxy)-2-methylimidazo[1,2-a]pyridine
mp: 140° to 141° C. (recrystallized from ethyl acetate)
IR (Nujol): 1280, 1100 cm$^{-1}$
NMR (CDCl$_3$, δ): 2.50 (3H, s), 5.36 (2H, s), 6.20–6.73 (2H, m), 7.10–7.80 (5H, m)

Preparation 13

A solution of 2-amino-3-(2-methylbenzylamino)pyridine (3.25 g) and chloroacetone (1.26 ml) in ethanol (65 ml) was refluxed for 18 hours and then evaporated in vacuo. To the residue was added aqueous sodium bicarbonate solution and the mixture was extracted with methylene chloride. The extract was washed with brine, dried over magnesium sulfate, and evaporated in vacuo. The oily residue was purified by column chromatography on silica gel (40 g) with a mixture of methylene chloride and ethyl acetate (10:1) as an eluent to give 8-(2-methylbenzylamino)-2-methylimidazo[1,2-a]pyridine (1.80 g).
NMR (CDCl$_3$, δ): 2.38 (3H, s), 2.42 (3H, s), 4.40 (2H, d, J=6 Hz), 5.06–5.46 (1H, broad s), 6.04 (1H, d, J=7.5 Hz), 6.56 (1H, t, J=7 Hz), 7.10–7.56 (6H, m)

Preparation 14

8-(2-Chlorobenzylamino)-2-methylimidazo[1,2-a]pyridine was obtained according to a similar manner to that of Preparation 13.
NMR (CDCl$_3$, δ): 2.43 (3H, s), 4.56 (2H, d, J=6 Hz), 5.36–5.76 (1H, m), 5.96 (1H, d, J=7 Hz), 6.52 (1H, t, J=7 Hz), 7.06–7.63 (6H, m).

Preparation 15

To a solution of 37% aqueous formaldehyde (2.38 g) in acetic acid (38 ml) was added dropwise 50% aqueous dimethylamine (2.63 g) with ice-cooling over a period of 10 minutes and the mixture was stirred for an additional 10 minutes. The mixture was heated at 50°–55° C. for 2 hours after an addition of 8-(2-chlorobenzyloxy)-2-methylimidazo[1,2-a]pyridine (7.6 g) thereto and then evaporated in vacuo. The residue was basified with aqueous sodium hydroxide and extracted with methylene chloride. The extract was washed with water, dried over magnesium sulfate and evaporated in vacuo. The residual solid was recrystallized from a mixture of diethyl ether and n-hexane to give 8-(2-chlorobenzyloxy)-3-dimethylaminomethyl-2-methylimidazo[1,2-a]pyridine (7.85 g).
mp: 100° to 101° C.
IR (Nujol): 1550, 1295, 1285 cm$^{-1}$
NMR (CDCl$_3$, δ): 2.26 (6H, s), 2.50 (3H, s), 3.63 (2H, s), 5.43 (2H, s), 6.30–6.80 (2H, m), 7.10–7.46 (3H, m), 7.50–7.93 (2H, m).

Preparation 16

The following compounds were obtained according to a similar manner to that of Preparation 15.
(1) 8-(2-Methylbenzyloxy)-3-dimethylaminomethyl-2-methylimidazo[1,2-a]pyridine
mp: 65° to 67° C. (recrystallized from petroleum ether)
IR (Nujol): 1535, 1270, 1085, 1010 cm$^{-1}$
NMR (CDCl$_3$, δ): 2.21 (6H, s), 2.40 (3H, s), 2.45 (3H, s), 3.60 (2H, s), 5.26 (2H, s), 6.30–6.77 (2H, m), 7.07–7.56 (4H, m), 7.81 (1H, dd, J=1.5 Hz and 6 Hz).
(2) 8-(1-Phenylethoxy)-3-dimethylaminomethyl-2-methylimidazo[1,2-a]pyridine
NMR (CDCl$_3$, δ): 1.80 (3H, d, J=7 Hz), 2.23 (6H, s), 2.50 (3H, s), 3.60 (2H, s), 5.50 (1H, q, J=7 Hz), 6.25 (1H, dd, J=1 Hz and 6 Hz), 6.46 (1H, t, J=6 Hz), 7.16–7.56 (5H, m), 7.71 (1H, dd, J=1 Hz and 6 Hz).
(3) 8-(3-Chlorobenzyloxy)-3-dimethylaminomethyl-2-methylimidazo[1,2-a]pyridine
mp: 71° to 72° C. (recrystallized from a mixture of of diethyl ether and n-hexane)
IR (Nujol): 1540, 1290, 1275 cm$^{-1}$
NMR (CDCl$_3$, δ): 2.22 (6H, s), 2.46 (3H, s), 3.63 (2H, s), 5.29 (2H, s), 6.30–6.79 (2H, m), 7.16–7.46 (3H, m), 7.52 (1H, s), 7.83 (1H, dd, J=2 Hz and 6 Hz).
(4) 8-(4-Chlorobenzyloxy)-3-dimethylaminomethyl-2-methylimidazo[1,2-a]pyridine
mp: 132° to 134° C.
NMR (DMSO-d$_6$, δ): 2.12 (6H, s), 2.30 (3H, s), 3.6 (2H, s), 5.25 (2H, s), 6.60–6.80 (2H, m), 7.45 (4H, s), 7.76–7.96 (1H, m).
(5) 8-(2-Bromobenzyloxy)-3-dimethylaminomethyl-2-methylimidazo[1,2-a]pyridine
mp: 107° to 108° C. (recrystallized from petroleum ether)
NMR (CDCl$_3$, δ): 2.22 (6H, s), 2.46 (3H, s), 3.60 (2H, s), 5.37 (2H, s), 6.27–6.73 (2H, m), 6.93–7.73 (4H, m), 7.80 (1H, dd, J=2 Hz and 6 Hz).
(6) 8-(2,6-Dichlorobenzyloxy)-3-dimethylaminomethyl-2-methylimidazo[1,2-a]pyridine
mp: 141° to 145° C.
NMR (CDCl$_3$, δ): 2.25 (6H, s), 2.45 (3H, s), 3.63 (2H, s), 5.50 (2H, s), 6.53–6.83 (2H, m), 7.16–7.50 (3H, m), 7.85 (1H, dd, J=3 Hz and 5 Hz).
(7) 8-(3,4-Dichlorobenzyloxy)-3-dimethylaminomethyl-2-methylimidazo[1,2-a]pyridine
mp: 96° to 98° C.
NMR (CDCl$_3$, δ): 2.23 (6H, s), 2.46 (3H, s), 3.60 (2H, s), 5.25 (2H, s), 6.36–6.80 (2H, m), 7.20–7.66 (3H, m), 7.83 (1H, dd, J=2 Hz and 7 Hz).
(8) 8(2,4-Dichlorobenzyloxy)-3-dimethylaminomethyl-2-methylimidazo[1,2-a]pyridine
mp: 90° to 92° C.
NMR (CDCl$_3$, δ): 2.23 (6H, s), 2.46 (3H, s), 3.63 (2H, s), 5.36 (2H, s), 6.26–6.76 (2H, m), 7.23 (1H, dd, J=2 Hz and 8 Hz), 7.40 (1H, d, J=2 Hz), 7.56 (1H, d, J=8 Hz), 7.80 (1H, dd, J=2 Hz and 7 Hz).
(9) 8-Benzyloxy-3-dimethylaminomethylimidazo[1,2-a]pyridine
mp: 86° to 87° C.
NMR (CDCl$_3$, δ): 2.23 (6H, s), 3.66 (2H, s), 5.33 (2H, s), 6.36–6.76 (2H, m), 7.20–7.60 (6H, m), 7.90 (1H, dd, J=2 Hz and 6 Hz).
(10) 8-Benzyloxy-3-dimethylaminomethyl-2-phenylimidazo[1,2-a]pyridine
mp: 87° to 89° C. (recrystallized from a mixture of ethyl acetate and n-hexane)

NMR (CDCl$_3$, δ): 2.23 (6H, s), 3.83 (2H, s), 5.40 (2H, s), 6.30–6.80 (2H, m), 7.20–8.13 (11H, m).

(11) 8-(2-Methylbenzylamino)-3-dimethylaminomethyl-2-methylimidazo[1,2-a]pyridine NMR (CDCl$_3$, δ): 2.22 (6H, s), 2.38 (6H, s), 3.58 (2H, s), 4.36 (2H, d, J=6 Hz), 5.0–5.43 (1H, broad s), 6.06 (1H, d, J=7 Hz), 6.59 (1H, t, J=7 Hz), 7.05–7.45 (4H, m), 7.55 (1H, d, J=7 Hz).

(12) 8-(2-Chlorobenzylamino)-3-dimethylaminomethyl-2-methylimidazo[1,2-a]pyridine NMR (CDCl$_3$, δ): 2.25 (6H, s), 2.45 (3H, s), 3.62 (2H, s), 4.60 (2H, d, J=6 Hz), 5.40–5.83 (1H, m), 6.03 (1H, d, J=7 Hz), 6.60 (1H, t, J=7 Hz), 7.07–7.56 (4H, m), 7.60 (1H, d, J=7 Hz).

Preparation 17

Methyl iodide (3.48 g) was added dropwise to a solution of 8-(2-chlorobenzyloxy)-3-dimethylaminomethyl-2-methylimidazo[1,2-a]pyridine (7.8 g) in acetone (100 ml) at room temperature and the mixture was stirred for 24 hours. The resulting precipitate was collected by filtration, washed with acetone, and dried in a desiccator to give 8-(2-chlorobenzyloxy)-3-trimethylammoniomethyl-2-methylimidazo[1,2-a]pyridine iodide (11.35 g).

mp: >165° C. (decomp.)

IR (Nujol): 1540, 1400, 1360, 1290 cm$^{-1}$

NMR (DMSO-d$_6$, δ): 2.50 (3H, s), 3.20 (9H, s), 5.10 (2H, s), 5.39 (2H, s), 6.98 (2H, broad d, J=4 Hz), 7.30–7.86 (4H, m), 8.55 (1H, broad-t, J=4 Hz).

Preparation 18

The following compounds were obtained according to a similar manner to that of Preparation 17.

(1) 8-(2-Methylbenzyloxy)-3-trimethylammoniomethyl-2-methylimidazo[1,2-a]pyridine iodide mp: >175° C. (decomp.)

IR (Nujol): 1545, 1490, 1285, 1270 cm$^{-1}$

NMR (DMSO-d$_6$, δ): 2.38 (3H, s), 2.46 (3H, s), 3.13 (9H, s), 5.02 (2H, s), 5.28 (2H, s), 6.9–7.6 (6H, m), 8.45 (1H, t, J=3.5 Hz).

(2) 8-(1-Phenylethoxy)-3-trimethylammoniomethyl-2-methylimidazo[1,2-a]pyridine iodide mp: 158° C. (decomp.)

NMR (DMSO-d$_6$, δ): 1.63 (3H, d, J=6 Hz), 2.49 (3H, s), 3.10 (9H, s), 4.96 (2H, s), 5.78 (1H, q, J=6 Hz), 6.53–7.0 (2H, m), 7.11–7.65 (5H, m), 8.35 (1H, broad d, J=6 Hz).

(3) 8-(3-Chlorobenzyloxy)-3-trimethylammoniomethyl-2-methylimidazo[1,2-a]pyridine iodide mp: >153° C. (decomp.)

IR (Nujol): 1540, 1290, 1080 cm$^{-1}$

NMR (DMSO-d$_6$, δ): 2.49 (3H, s), 3.16 (9H, s), 5.06 (2H, s), 5.39 (2H, s), 6.86–7.1 (2H, m), 7.33–7.73 (4H, m), 8.40–8.63 (1H, m).

(4) 8-(4-Chlorobenzyloxy)-3-trimethylammoniomethyl-2-methylimidazo[1,2-a]pyridine iodide mp: >180° C. (decomp.)

NMR (DMSO-d$_6$, δ): 2.52 (2H, s), 3.22 (9H, s), 5.10 (2H, s), 5.33 (2H, s), 6.80–7.10 (2H, m), 7.30–7.70 (4H, m), 8.54 (1H, broad t, J=3 Hz).

(5) 8-(2-Bromobenzyloxy)-3-trimethylammoniomethyl-2-methylimidazo[1,2-a]pyridine iodide mp: >160° C. (decomp.)

NMR (DMSO-d$_6$, δ): 2.47 (3H, s), 3.14 (9H, s), 5.01 (2H, s), 5.32 (2H, s), 6.86–7.06 (2H, m), 7.23–7.86 (4H, m), 8.36–8.63 (1H, m).

(6) 8-(2,6-Dichlorobenzyloxy)-3-trimethylammoniomethyl-2-methylimidazo[1,2-a]pyridine iodide mp: 270° to 275° C. (decomp.)

NMR (DMSO-d$_6$, δ): 2.40 (3H, s), 3.10 (9H, s), 5.00 (2H, s), 5.40 (2H, s), 6.76–7.20 (2H, m), 7.40–7.70 (3H, m), 8.45 (1H, dd, J=2 Hz and 6 Hz).

(7) 8-(3,4-Dichlorobenzyloxy)-3-trimethylammoniomethyl-2-methylimidazo[1,2-a]pyridine iodide mp: 190° C. (decomp.)

NMR (DMSO-d$_6$, δ): 2.43 (3H, s), 3.13 (9H, s), 5.00 (2H, s), 5.45 (2H, s), 6.46–6.76 (2H, m), 7.36–7.83 (3H, m), 8.45 (1H, dd, J=2 Hz and 4 Hz).

(8) 8-(2,4-Dichlorobenzyloxy)-3-trimethylammoniomethyl-2-methylimidazo[1,2-a]pyridine iodide mp: 187° C. (decomp.)

NMR (DMSO-d$_6$, δ): 2.50 (3H, s), 3.20 (9H, s), 5.03 (2H, s), 5.35 (2H, s), 6.86–7.10 (2H, m), 7.50 (1H, dd, J=2 Hz and 8 Hz), 7.68 (1H, d, J=2 Hz), 7.75 (1H, d, J=8 Hz), 8.43–8.63 (1H, m).

(9) 8-Benzyloxy-3-trimethylammoniomethylimidazo[1,2-a]pyridine iodide mp: 202° C. (decomp.)

NMR (DMSO-d$_6$, δ): 3.16 (9H, s), 5.10 (2H, s), 5.36 (2H, s), 6.70–7.20 (2H, m), 7.26–7.73 (5H, m), 7.86 (1H, s), 8.56 (1H, dd, J=2 Hz and 6 Hz).

(10) 8-Benzyloxy-3-trimethylammoniomethyl-2-phenylimidazo[1,2-a]pyridine iodide mp: 159° C. (decomp.)

NMR (DMSO-d$_6$, δ): 2.90 (9H, s), 5.23 (2H, s), 5.33 (2H, s), 6.90–7.10 (2H, m), 7.23–8.00 (10H, m), 8.56 (1H, dd, J=3 Hz and 5 Hz).

(11) 8-(2-Methylbenzylamino)-3-trimethylammoniomethyl-2-methylimidazo[1,2-a]pyridine iodide mp: 190° C. (decomp.)

NMR (DMSO-d$_6$, δ): 2.35 (3H, s), ca. 2.4–2.7 (3H, s), 3.12 (9H, s), 4.45 (2H, d, J=6 Hz), 4.85 (2H, s), 6.08 (1H, d, J=8 Hz), 6.35–6.95 (2H, m), 7.06–7.36 (4H, m), 8.03 (1H, d, J=7 Hz).

(12) 8-(2-Chlorobenzylamino)-3-trimethylammoniomethyl-2-methylimidazo[1,2-a]pyridine iodide mp: >140° C. (decomp.)

NMR (DMSO-d$_6$, δ): 2.53 (3H, s), 3.16 (9H, s), 4.55 (2H, d, J=6 Hz), 4.98 (2H, s), 6.03 (1H, d, J=8 Hz), 6.56–6.93 (2H, m), 7.10–7.63 (4H, m), 8.11 (1H, d, J=7 Hz).

EXAMPLE 1

A solution of 2-amino-3-benzyloxypyridine (3 g) and 3-chloro-5-hexen-2-one (2.981 g) in ethanol (15 ml) was stirred and refluxed for 45 hours and then evaporated in vacuo. To the residue was added an aqueous solution of sodium bicarbonate and the mixture was extracted with ethyl acetate. The extract was washed with water, dried over magnesium sulfate and evaporated in vacuo. The oily residue was purified by column chromatography on silica gel (50 g) using methylene chloride and then chloroform as eluents. The eluate with chloroform was evaporated in vacuo and the residual solid was recrystallized from diisopropyl ether to give 8-benzyloxy-3-allyl-2-methylimidazo[1,2-a]pyridine (0.31 g).

mp: 90.5° to 91.5° C.

IR (Nujol): 1530, 1275 cm$^{-1}$

NMR (CDCl$_3$, δ): 2.43 (3H, s), 3.43–3.66 (2H, m), 4.69–5.20 (2H, m), 5.30 (2H, s), ca. 5.4–6.2 (1H, m), 6.23–6.69 (2H, m), 7.13–7.58 (6H, m).

Analysis Calcd. for C$_{18}$H$_{18}$N$_2$O: C: 77.67; H: 6.52; N: 10.06. Found: C: 78.06; H: 6.61; N: 9.94.

EXAMPLE 2

A solution of 2-amino-3-benzyloxypyridine (2 g) and 3-tosyloxy-5-hexyn-2-one (2.66 g) in ethanol (15 ml) was stirred and refluxed for 24 hours and then evaporated in vacuo. To the residue was added an aqueous solution of sodium bicarbonate and the mixture was extracted with ethyl acetate. The extract was washed with water, dried over magnesium sulfate and evaporated in vacuo. The oily residue was purified by column chromatography on silica gel (50 g) using chloroform as an eluent to give a solid, which was recrystallized from a mixture of methylene chloride and diethyl ether to give 8-benzyloxy-3-(2-propynyl)-2-methylimidazo[1,2-a]pyridine (0.855 g).

mp: 112° to 112.5° C.

IR (Nujol): 3270, 1570, 1535, 1280, 1265, 1085, 1010 cm$^{-1}$

NMR (CDCl$_3$, δ): 2.05 (1H, t, J=3 Hz), 2.48 (3H, s), 3.73 (2H, d, J=3 Hz), 5.33 (2H, s), 6.31–6.78 (2H, m), 7.20–7.76 (6H, m).

Analysis Calcd. for C$_{18}$H$_{16}$N$_2$O: C: 78.24; H: 5.84: N: 10.14. Found: C: 78.40; H: 5.72; N: 10.30.

EXAMPLE 3

8-(2-Phenylethoxy)-3-(2-propynyl)-2-methylimidazo[1,2-a]pyridine was obtained by reacting 2-amino-3-(2-phenylethoxy)pyridine with 3-mesyloxy-5-hexyn-2-one according to similar manners to those of Examples 1 and 2.

mp: 114° to 116° C. (recrystallized from a mixture of ethyl acetate and n-hexane)

IR (Nujol): 3295, 3095, 2100 cm$^{-1}$

NMR (CDCl$_3$, δ): 2.07 (1H, t, J=3 Hz), 2.49 (3H, s), 3.30 (2H, t, J=8 Hz), 3.76 (2H, d, J=3 Hz), 4.37 (2H, t, J=8 Hz), 6.33–6.86 (2H, m), 7.30 (5H, s), 7.68 (1H, dd, J=1 Hz and 7 Hz).

Analysis Calcd. for C$_{19}$H$_{18}$N$_2$O: C: 78.59; H: 6.25; N: 9.65. Found: C: 78.43; H: 6.11; N: 9.98.

EXAMPLE 4

A solution of 2-amino-3-(2-methylbenzyloxy)pyridine (5 g) and 3-tosyloxy-5-hexyn-2-one (7.45 g) in ethanol (35 ml) was heated under reflux for 28 hours and then evaporated in vacuo. The residue was dissolved in ethyl acetate and the solution was allowed to stand at ambient temperature. The resultant precipitate was collected by filtration and dissolved in a mixture of methylene chloride and aqueous sodium bicarbonate. The organic layer was separated, washed with saturated sodium chloride aqueous solution, treated with silica gel and activated charcoal successively, and evaporated in vacuo.

The crystalline residue was recrystallized from ethyl acetate to give 8-(2-methylbenzyloxy)-3-(2-propynyl)-2-methylimidazo[1,2-a]pyridine (1.44 g).

mp: 138° to 140° C.

IR (Nujol): 3270, 1570, 1535 cm$^{-1}$

NMR (CDCl$_3$, δ): 2.04 (1H, t, J=3 Hz), 2.38 (3H, s), 2.44 (3H, s), 3.75 (2H, d, J=3 Hz), 5.28 (2H, s), 6.45 (1H, dd, J=1 Hz and 8 Hz), 6.66 (1H, t, J=8 Hz), 7.06–7.30 (3H, m), 7.37–7.55 (1H, m), 7.70 (1H, dd, J=1 Hz and 8 Hz)

Analysis, Calcd. for C$_{19}$H$_{18}$N$_2$O: C: 78.59; H: 6.25; N: 9.65. Found: C: 78.69; H: 6.11; N: 9.74.

EXAMPLE 5

The following compounds were prepared according to similar manners to those of Examples 1, 2, 3 and 4.

(1) 8-(2-Ethylbenzyloxy)-3-(2-propynyl)-2-methylimidazo[1,2-a]pyridine mp: 109° to 110° C. (recrystallized from a mixture of ethyl acetate and n-hexane)

IR (Nujol): 3275 cm$^{-1}$

NMR (CDCl$_3$, δ): 1.24 (3H, t, J=8 Hz), 2.03 (1H, t, J=3 Hz), 2.43 (3H, s), 2.76 (2H, q, J=8 Hz), 3.74 (2H, d, J=3 Hz), 5.31 (2H, s), 6.49 (1H, d, J=7 Hz), 6.68 (1H, t, J=7 Hz), 7.13–7.43 (3H, m), 7.49–7.66 (1H, m), 7.81 (1H, d, J=7 Hz).

Analysis Calcd. for C$_{20}$H$_{20}$N$_2$O: C: 78.92; H: 6.62; N: 9.20. Found: C: 79.13; H: 6.39; N: 9.23.

(2) 8-(2-Isopropylbenzyloxy)-3-(2-propynyl)-2-methylimidazo[1,2-a]pyridine mp: 108° to 109° C. (recrystallized from a mixture of ethyl acetate and n-hexane)

IR (Nujol): 3280 cm$^{-1}$

NMR (CDCl$_3$, δ): 1.26 (6H, d, J=7 Hz), 2.03 (1H, t, J=3 Hz), 2.43 (3H, s), 3.32 (1H, septet, J=7 Hz), 3.74 (2H, d, J=3 Hz), 5.36 (2H, s), 6.45 (1H, d, J=7 Hz), 6.66 (1H, t, J=7 Hz), 7.00–7.53 (4H, m), 7.69 (1H, d, J=7 Hz).

Analysis, Calcd. for C$_{21}$H$_{22}$N$_2$O: C: 79.21; H: 6.96; N: 8.80. Found: C: 79.32; H: 7.38; N: 8.68.

(3) 8-(2-Chlorobenzyloxy)-3-(2-propynyl)-2-methylimidazo[1,2-a]pyridine mp: 130° to 131° C. (recrystallized from ethyl acetate)

IR (Nujol): 3265, 1560, 1525 cm$^{-1}$

NMR (CDCl$_3$, δ): 2.05 (1H, t, J=3 Hz), 2.46 (3H, s), 3.76 (2H, d, J=3 Hz), 5.42 (2H, s), 6.42 (1H, d, J=7 Hz), 6.66 (1H, t, J=7 Hz), 7.15–7.50 (3H, m), 7.53–7.70 (1H, m), 7.72 (1H, d, J=7 Hz)

Analysis, Calcd. for C$_{18}$H$_{15}$ClN$_2$O: C: 69.57; H: 4.86; N: 9.01. Found: C: 69.58; H: 5.13; N: 9.06.

(4) 8-(3-Chlorobenzyloxy)-3-(2-propynyl)-2-methylimidazo[1,2-a]pyridine.

mp: 110° to 111° C. (recrystallized from a mixture of ethyl acetate and n-hexane)

IR (Nujol): 3200, 1542 cm$^{-1}$

NMR (CDCl$_3$, δ): 2.04 (1H, t, J=3 Hz), 2.46 (3H, s), 3.76 (2H, d, J=3 Hz), 5.29 (2H, s), 6.43 (1H, d, J=7 Hz), 6.66 (1H, t, J=7 Hz), 7.18–7.40 (3H, m), 7.49 (1H, s), 7.71 (1H, d, J=7 Hz)

Analysis Calcd. for C$_{18}$H$_{15}$ClN$_2$O: C: 69.57; H: 4.86; N: 9.11. Found: C: 69.86; H: 4.79; N: 9.11.

(5) 8-(4-Chlorobenzyloxy)-3-(2-propynyl)-2-methylimidazo[1,2-a]pyridine mp: 173° to 175° C. (recrystallized from ethyl acetate)

IR (Nujol): 3295 cm$^{-1}$

NMR (CDCl$_3$, δ): 2.05 (1H, t, J=3 Hz), 2.48 (3H, s), 3.76 (2H, d, J=3 Hz), 5.30 (2H, s), 6.32–6.83 (2H, m), 7.19–7.56 (4H, m), 7.72 (1H, dd, J=2 Hz, 6 Hz)

Analysis Calcd. for C$_{18}$H$_{15}$ClN$_2$O: C: 69.57; H: 4.86; N: 9.01. Found: C: 69.45; H: 4.55; N: 9.18.

(6) 8-(2-Bromobenzyloxy)-3-(2-propynyl)-2-methylimidazo[1,2-a]pyridine mp: 156° to 157° C. (recrystallized from ethyl acetate)

IR (Nujol): 3150, 2100, 1535 cm$^{-1}$

NMR (CDCl$_3$, δ): 2.0–2.17 (1H, m), 2.46 (3H, s), 3.76 (2H, d, J=3 Hz), 5.38 (2H, s), 6.40 (1H, d, J=7.5 Hz), 6.65 (1H, t, J=7.5 Hz), 7.03–7.40 (2H, m), 7.50–7.80 (3H, m)

Analysis Calcd. for C$_{18}$H$_{15}$BrN$_2$O: C: 60.86; H: 4.26; N: 7.89. Found: C: 61.01; H: 4.45; N: 7.84.

(7) 8-(2-Fluorobenzyloxy)-3-(2-propynyl)-2-methylimidazo[1,2-a]pyridine mp: 123° to 125° C. (recrystallized from a mixture to ethyl acetate and n-hexane)

IR (Nujol): 3300, 3275 cm$^{-1}$

NMR (CDCl$_3$, δ): 2.06 (1H, t, J=3 Hz), 2.49 (3H, s), 3.77 (2H, d, J=3 Hz), 5.40 (2H, s), 6.52 (1H, d, J=7 Hz), 6.69 (1H, t, J=7 Hz), 6.92–7.63 (4H, m), 7.73 (1H, d, J=7 Hz).

Analysis, Calcd. for C$_{18}$H$_{15}$FN$_2$O: C: 73.45; H: 5.14; N: 9.52. Found: C: 73.72; H: 5.02; N: 9.45.

(8) 8-(2,6-Dimethylbenzyloxy)-3-(2-propynyl)-2-methylimidazo[1,2-a]pyridine mp: 165° to 168° C. (recrystallized from a mixture of ethanol and n-hexane)

IR (Nujol): 3185 cm$^{-1}$

NMR (CDCl$_3$, δ): 2.06 (1H, t, J=3 Hz), 2.39 and 2.40 (each s, total 9H), 3.76 (2H, d, J=3 Hz), 5.23 (2H, s), 6.53–6.87 (2H, m), 6.94–7.28 (3H, m), 7.73 (1H, dd, J=2 Hz and 7 Hz)

Analysis Calcd. for C$_{20}$H$_{20}$N$_2$O: C: 78.92; H: 6.62; N: 9.20. Found: C: 78.95; H: 6.38; N: 9.06.

(9) 8-(2,6-Dichlorobenzyloxy)-3-(2-propynyl)-2-methylimidazo[1,2-a]pyridine mp: 183° to 184° C. (decomp.) (recrystallized from a mixture of methylene chloride and diisopropyl ether)

IR (Nujol): 3180, 1540 cm$^{-1}$

NMR (CDCl$_3$, δ): 2.06 (1H, t, J=3 Hz), 2.43 (3H, s), 3.75 (2H, d, J=3 Hz), 5.47 (2H, s), 6.57–6.89 (2H, m), 7.17–7.43 (3H, m) 7.76 (1H, dd, J=2 Hz and 7 Hz).

Analysis Calcd. for C$_{18}$H$_{14}$Cl$_2$N$_2$O: C: 62.62; H: 4.09; N: 8.11. Found: C: 63.14; H: 4.29; N: 8.17.

(10) 8-(2-Naphthylmethoxy)-3-(2-propynyl)-2-methylimidazo[1,2-a]pyridine mp: 138° to 139° C. (recrystallized from a mixture of ethyl acetate and n-hexane)

IR (Nujol): 3290 cm$^{-1}$

NMR (CDCl$_3$, δ): 2.04 (1H, t, J=3 Hz), 2.50 (3H, s), 3.74 (2H, d, J=3 Hz), 5.50 (2H, s), 6.33–6.78 (2H, m), 7.23–8.01 (8H, m)

(11) 8-(1-Naphthylmethoxy)-3-(2-propynyl)-2-methylimidazo[1,2-a]pyridine mp: 138° to 139° C. (recrystallized from a mixture of ethyl acetate and n-hexane)

IR (Nujol): 3175, 2100 cm$^{-1}$

NMR (CDCl$_3$, δ): 2.05 (1H, t, J=3 Hz), 2.46 (3H, s), 3.75 (2H, d, J=3 Hz), 5.80 (2H, s), 6.42–6.82 (2H, m), 7.22–8.26 (8H, m).

Analysis Calcd. for C$_{22}$H$_{18}$N$_2$O: C: 80.96; H: 5.56; N: 8.58. Found: C: 80.86; H: 5.62; N: 8.86.

(12) 8-(1,2,3,4-Tetrahydro-1-naphthyloxy)-3-(2-propynyl)-2-methylimidazo[1,2-a]pyridine mp: 139° to 141° C. (recrystallized from a mixture of ethanol and n-hexane)

IR (Nujol): 3180 cm$^{-1}$

NMR (CDCl$_3$, δ): 1.67–2.34 (5H, m), 2.44 (3H, s), 2.83–2.97 (2H, m), 3.78 (2H, d, J=3 Hz), 5.79 (1H, broad t, J=4 Hz), 6.57–6.89 (2H, m), 7.01–7.30 (3H, m), 7.36–7.54 (1H, m), 7.74 (1H, dd, J=2 Hz and 7 Hz).

Analysis Calcd. for C$_{21}$H$_{20}$N$_2$O.½H$_2$O: C: 77.51; H: 6.50; N: 8.61. Found: C: 78.08; H: 6.46; N: 8.66.

(13) 8-(Cinnamyloxy)-3-(2-propynyl)-2-methylimidazo[1,2-a]pyridine (trans isomer)

mp: 130° to 131° C. (recrystallized from a mixture of ethyl acetate and n-hexane)

IR (Nujol): 3280 cm$^{-1}$

NMR (CDCl$_3$, δ): 2.04 (1H, t, J=3 Hz), 2.44 (3H, s), 3.75 (2H, d, J=3 Hz), 4.91 (2H, d, J=5 Hz), 6.28–6.90 (4H, m), 7.14–7.44 (5H, m), 7.71 (1H, d, J=7.5 Hz)

Analysis Calcd. for C$_{20}$H$_{18}$N$_2$O: C: 79.44; H: 6.00; N: 9.26. Found: C: 79.26; H: 6.10; N: 9.24.

(14) 8-Cyclohexylmethoxy-3-(2-propynyl)-2-methylimidazo[1,2-a]pyridine mp: 118° to 119.5° C. (recrystallized from a mixture of ethyl acetate and n-hexane)

IR (Nujol): 3200, 2100 cm$^{-1}$

NMR (CDCl$_3$, δ): 0.83–2.26 (11H, m), 2.03 (1H, t, J=3 Hz), 2.46 (3H, s), 3.80 (2H, d, J=3 Hz), 3.98 (2H, d, J=6 Hz), 6.48 (1H, d, J=7 Hz), 6.73 (1H, t, J=7 Hz), 7.71 (1H, dd, J=1 Hz and 7 Hz).

Analysis Calcd. for C$_{18}$H$_{22}$N$_2$O: C: 76.56; H: 7.85; N: 9.92. Found: C: 77.05; H: 7.54; N: 9.80.

(15) 8-Ethoxy-3-(2-propynyl)-2-methylimidazo[1,2-a]pyridine mp: 163° to 165° C. (recrystallized from a mixture of ethyl acetate and n-hexane)

IR (Nujol): 3190, 2100 cm$^{-1}$

NMR (CDCl$_3$, δ): 1.53 (3H, t, J=7 Hz), 2.03 (1H, t, J=3 Hz), 2.44 (3H, s), 3.73 (2H, d, J=3 Hz), 4.20 (2H, q, J=7 Hz), 6.40 (1H, d, J=7 Hz), 6.66 (1H, t, J=7 Hz), 7.65 (1H, dd, J=1 Hz and 7 Hz).

Analysis Calcd. for C$_{13}$H$_{14}$N$_2$O: C: 72.87; H: 6.59; N: 13.07. Found: C: 73.04; H: 6.48; N: 13.26.

(16) 8-(2-Methylbenzyloxy)-3-(1,2-propadienyl)-2-methylimidazo[1,2-a]pyridine mp: 88° to 89° C. (recrystallized from a mixture of diethyl ether and petroleum ether)

IR (Nujol): 1930 cm$^{-1}$

(17) 8-Benzyloxy-3-(2-propynyloxymethyl)-2-methylimidazo[1,2-a]pyridine hydrochloride mp: 167° to 169° C.

IR (Nujol): 3180, 2560 (broad), 2125, 1675, 1580, 1090 cm$^{-1}$

(18) 8-Benzyloxy-3-(2-propynyloxymethyl)-2-methylimidazo[1,2-a]pyridine mp: 103° to 104° C.

IR (Nujol): 3250, 2125, 1545, 1470, 1075 cm$^{-1}$

(19) 8-(1-Phenylethoxy)-3-(2-propynyloxymethyl)-2-methylimidazo[1,2-a]pyridine

IR (film/NaCl): 2100 cm$^{-1}$

(20) 8-(2-Methylbenzyloxy)-3-(2-propynyloxymethyl)-2-methylimidazo[1,2-a]pyridine mp: 87° to 89° C.

IR (Nujol): 3225, 2125, 1530, 1060, 1050 cm$^{-1}$

(21) 8-(2-Chlorobenzyloxy)-3-(2-propynyloxymethyl)-2-methylimidazo[1,2-a]pyridine mp: 95° to 95.5° C.

IR (Nujol): 3280, 2120, 1575, 1545, 1295, 1070 cm$^{-1}$

(22) 8-(3-Chlorobenzyloxy)-3-(2-propynyloxymethyl)-2-methylimidazo[1,2-a]pyridine mp: 81° to 83° C. (recrystallized from petroleum ether)

IR (Nujol): 3130, 2095, 1570, 1540, 1285, 1055 cm$^{-1}$

(23) 8-(4-Chlorobenzyloxy)-3-(2-propynyloxymethyl)2-methylimidazo[1,2-a]pryridine mp: 130° to 131° C. (recrystallized from a mixture of ethyl acetate and n-hexane)

IR (Nujol): 3240, 2100, 1530, 1490, 1360, 1275, 1265 cm$^{-1}$

(24) 8-(2-Bromobenzyloxy)-3-(2-propynyloxymethyl)-2-methylimidazo[1,2-a]pyridine mp: 103° to 104° C. (recrystallized from a mixture of methylene chloride and diethyl ether)

(25) 8-(2,6-Dichlorobenzyloxy)-3-(2-propynyloxymethyl)-2-methylimidazo[1,2-a]pyridine mp: 129° to 130° C. (recrystallized from a mixture of ethyl acetate and n-hexane)

IR (Nujol): 3290 cm$^{-1}$

(26) 8-(3,4-Dichlorobenzyloxy)-3-(2-propynyloxymethyl)-2-methylimidazo]1,2-a]pyridine
mp: 105° to 107° C. (recrystallized from a mixture of ethyl acetate and n-hexane)
IR (Nujol): 3260, 2110, 1280, 1160 cm$^{-1}$

(27) 8-(2,4-Dichlorobenzyloxy)-3-(2-propynyloxymethyl)-2-methylimidazo[1,2-a]pyridine
mp: 123° to 124° C. (recrystallized from a mixture of ethyl acetate and n-hexane)
IR (Nujol): 3250, 2110, 1280, 1060 cm$^{-1}$

(28) 8-Benzyloxy-3-(2-propynyloxymethyl)imidazo[1,2-a]pyridine
mp: 84° to 85° C. (recrystallized from diisopropyl ether)
IR (Nujol): 3170, 2100 cm$^{-1}$

(29) 8-Benzyloxy-3-(2-propynyloxymethyl)-2-phenylimidazo[1,2-a]pyridine
NMR (CDCl$_3$, δ): 2.40 (1H, t, J=1 Hz), 4.20 (2H, d, J=1 Hz), 4.96 (2H, s), 5.33 (2H, s), 6.40–6.80 (2H, m), 7.20–7.70 (8H, m), 7.76–7.96 (3H, m).

(30) 8-(2-Methylbenzylamino)-3-(2-propynyloxymethyl)-2-methylimidazo[1,2-a]pyridine hydrochloride
mp: 159° to 161° C. (recrystallized from a mixture of ethanol and n-hexane)

(31) 8-(2-Chlorobenzylamino)-3-(2-propynyloxymethyl)-2-methylimidazo[1,2-a]pyridine hydrochloride
mp: 169° C. (decomp.) (recrystallized from a mixture of ethanol and diethyl ether)

(32) 8-Benzyloxy-3-allyloxymethyl-2-methylimidazo[1,2-a]pyridine
mp: 70° to 71° C.
IR (Nujol): 1535, 1280, 1265, 1195, 1100, 1050, 1015 cm$^{-1}$

(33) 8-Benzyloxy-3-(3-carboxy-2-propynyloxymethyl)-2-methylimidazo[1,2-a]pyridine
mp: 151° C. (decomp.)

(34) 8-Benzyloxy-3-(3-ethoxycarbonyl-2-propynyloxymethyl)-2-methylimidazo[1,2-a]pyridine
NMR (CDCl$_3$, δ): 1.33 (3H, t, J=5 Hz), 2.53 (3H, s), 4.20 (2H, s), 4.27 (2H, q, J=5 Hz), 4.90 (2H, s), 5.30 (2H, s), 6.50 (1H, dd, J=1 Hz and 5 Hz), 6.65 (1H, t, J=5 Hz), 7.26–7.60 (5H, m), 7.75 (1H, dd, J=1 Hz and 5 Hz).

EXAMPLE 6

A solution of 2-amino-3-(2-methylbenzylamino)pyridine (2 g) and 3-mesyloxy-5-hexyn-2-one (1.78 g) in ethanol (40 ml) was refluxed for 31.5 hours and then evaporated in vacuo. The residue was treated with aqueous sodium bicarbonate solution and extracted with methylene chloride. The extract was washed with water, dried over magnesium sulfate, and evaporated in vacuo. The residue was purified by column chromatography on silica gel (40 g) with a mixtutre of methylene chloride and ethyl acetate (50:1 to 10:1) as an eluent to give 8-(2-methylbenzylamino)-3-(2-propynyl)-2-methylimidazo[1,2-a]pyridine (0.82 g).
mp: 126° to 128° C. (recrystallized from diisopropyl ether)
NMR (CDCl$_3$, δ): 2.04 (1H, t, J=3 Hz), 2.38 (3H, s), 2.40 (3H, s), 3.73 (2H, d, J=3 Hz), 4.39 (2H, d, J=5 Hz), 5.13–5.43 (1H, broad s), 6.08 (1H, d, J=8 Hz), 6.66 (1H, t, J=7 Hz), 7.0–7.43 (4H, m), 7.45 (1H, d, J=6 Hz).

EXAMPLE 7

8-(2-Chlorobenzylamino)-3-(2-propynyl)-2-methylimidazo[1,2-a]pyridine was obtained according to a similar manner to that of Example 6.
mp: 115° to 116.5° C. (recrystallized from a mixture of ethyl acetate and n-hexane)
NMR (CDCl$_3$, δ): 2.03 (1H, t, J=3 Hz), 2.40 (3H, s), 3.68 (2H, d, J=3 Hz), 4.52 (2H, d, J=6 Hz), 5.55 (1H, broad t, J=6 Hz), 5.95 (1H, d, J=7 Hz), 6.55 (1H, t, J=7 Hz), 6.96–7.55 (5H, m).
Analysis Calcd. for C$_{18}$H$_{16}$ClN$_3$: C: 69.79; H: 5.21; N: 13.56. Found: C: 69.97; H: 5.48; N: 13.62.

EXAMPLE 8

Sodium bicarbonate (2.73 g) was added to a solution of 2-amino-3-(2-methylbenzyloxy)pyrazine (3.5 g) and 3-mesyloxy-5-hexyn-2-one (6.18 g) in ethanol (35 ml) and the mixture was refluxed for 12 hours. The mixture was poured into an aqueous solution of sodium bicarbonate and extracted with chloroform. The extract was washed with water, dried over magnesium sulfate, and evaporated in vacuo. The residue was purified by column chromatography on silica gel (200 g) with a mixture of chloroform and methanol (50:1) as an eluent to give 8-(2-methylbenzyloxy)-3-(2-propynyl)-2-methylimidazo[1,2-a]pyrazine (0.182 g).
mp: 123° to 124° C.
NMR (CDCl$_3$, δ): 2.08 (1H, t, J=3 Hz), 2.42 (3H, s), 2.45 (3H, s), 3.72 (2H, d, J=3 Hz), 5.55 (2H, s), 7.00–7.55 (4H, m), 7.35 (1H, d, J=5 Hz), 7.63 (1H, d, J=5 Hz).

EXAMPLE 9

8-(2-Methylbenzylamino)-3-(2-propynyl)-2-methylimidazo[1,2-a]pyrazine hydrochloride was obtained according to a similar manner to that of Example 8.
mp: 184° to 186° C. (decomp.)
Analysis Calcd. for C$_{18}$H$_{18}$N$_4$.HCl: C: 66.19; H: 5.95; N: 17.38; Cl: 10.90. Found: C: 66.15; H: 5.86; N: 17.14; Cl: 10.52.
IR (Nujol): 3350, 3180, 2560, 1660, 1635, 1525 cm$^{-1}$
NMR (DMSO-d$_6$, δ): 2.37 (3H, s), ca. 2.3–2.7 (3H, s), 3.13 (1H, t, J=3 Hz), 4.08 (2H, d, J=3 Hz), 4.90 (2H, d, J=6 Hz), 7.00–7.50 (4H, m), 7.42 (1H, d, J=5 Hz), 7.92 (1H, d, J=5 Hz), 9.70–10.2 (1H, broad).

EXAMPLE 10

A solution of 8-(2-methylbenzyloxy)-3-(2-propynyl)-2-methylimidazo[1,2-a]pyridine (0.99 g) and 1N-sodium hydroxide solution (5.65 ml) in methanol (50 ml) was stirred for 72 hours at room temperature. The mixture was evaporated in vacuo and the residue was dissolved in chloroform. The solution was washed with brine, dried over magnesium sulfate, and evaporated in vacuo. The residue was purified by column chromatography on silica gel (14 g) with a mixture of chloroform and ethyl acetate (15:1) as an eluent to give 8-(2-methylbenzyloxy)-3-(1,2-propadienyl)-2-methylimidazo[1,2-a]pyridine (0.27 g).
mp: 88° to 89° C. (recrystallized from a mixture of diethyl ether and petroleum ether).
IR (Nujol): 1930 cm$^{-1}$
NMR (CDCl$_3$, δ): 2.40 (3H, s), 2.46 (3H, s), 5.26 (2H, s), 5.26–5.43 (2H, m), 6.40–6.76 (3H, m), 7.06–7.30 (3H, m), 7.33–7.53 (1H, m), 8.10 (1H, dd, J=1 Hz and 7 Hz).
Analysis Calcd. for C$_{19}$H$_{18}$N$_2$O: C: 78.59; H: 6.25; N: 9.65. Found: C: 78.86; H: 6.02; N: 9.57.

EXAMPLE 11

To a solution of sodium hydride (61% in mineral oil dispersion) (7.39 g) in 2-propynyl alcohol (300 ml) was added 8-benzyloxy-3-trimethylammoniomethyl-2- methylimidazo[1,2-a]pyridine iodine (74.6 g), and the mixture was heated at 90°–95° C. with stirring for 2.5 hours. After being cooled, the mixture was evaporated in vacuo and the residue was dissolved in methylene chloride. The solution was washed with water, dried over magnesium sulfate, and evaporated in vacuo. The oily residue was purified by column chromatography on silica gel (200 g) with methylene chloride as an eluent and the fractions containing the object compound were combined. The resultant solution was treated with a solution of hydrogen chloride in ethanol to give 8-benzyloxy-3-(2-propynyloxymethyl)-2-methylimidazo[1,2-a]pyridine hydrochloride (37.5 g).

mp: 167° to 169° C.

IR (Nujol): 3180, 2560 (broad), 2125, 1675, 1580, 1090 cm$^{-1}$

NMR (D$_2$O, δ): 2.56 (3H, s), 3.03 (1H, t, J=2 Hz), 4.31 (2H, d, J=2 Hz), 4.96 (2H, s), 5.29 (2H, s), 7.13–7.56 (7H, m), 8.01–8.14 (1H, m).

Analysis Calcd. for C$_{19}$H$_{19}$ClN$_2$O$_2$: C: 66.57; H: 5.59; N: 8.17. Found: C: 66.37; H: 5.33; N: 8.06.

EXAMPLE 12

A solution of 8-benzyloxy-3-(2-propynyloxymethyl)-2-methylimidazo[1,2-a]pyridine hydrochloride (35.5 g) in hot water (700 ml) was neutralized with aqueous sodium hydroxide solution and extracted with methylene chloride. The extract was washed with water, dried over magnesium sulfate, treated with activated charcoal, and evaporated in vacuo. The residual solid was recrystallized from a mixture of methylene chloride and n-hexane to give 8-benzyloxy-3-(2-propynyloxymethyl)-2-methylimidazo[1,2-a]pyridine (26.03 g).

mp: 103° to 104° C.

IR (Nujol): 3250, 2125, 1545, 1470, 1075 cm$^{-1}$

NMR (CDCl$_3$, δ): 2.43–2.60 (1H, m), 2.53 (3H, s), 4.07 (2H, d, J=2 Hz), 4.87 (2H, s), 5.33 (2H, s), 6.33–6.76 (2H, m), 7.20–7.60 (5H, m), 7.73 (1H, dd, J=2 Hz and 6 Hz).

EXAMPLE 13

To a solution of sodium hydride (63.6% in mineral oil dispersion, 0.285 g) in 2-propynyl alcohol (12 ml) was added 8-(2-methylbenzyloxy)-3-trimethylammoniomethyl-2-methylimidazo[1,2-a]pyridine iodide (3 g) and the mixture was heated at 85°–100° C. for 1.5 hours. After being cooled, the mixture was poured into ice-water and the resulting precipitate was collected by filtration and dissolved in methylene chloride. The solution was treated successively with silica gel (4.5 g) and activated charcoal and evaporated in vacuo. The crystalline residue was recrystallized from a mixture of ethyl acetate and petroleum ether to give 8-(2-methylbenzyloxy)-3-(2-propynyloxymethyl)-2-methylimidazo[1,2-a]pyridine (1.18 g).

mp: 87° to 89° C.

IR (Nujol): 3225, 2125, 1530, 1060, 1050 cm$^{-1}$

NMR (CDCl$_3$, δ): ca. 2.3–2.6 (1H), 2.40 (3H, s), 2.50 (3H, s), 4.06 (2H, d, J=2 Hz), 4.86 (2H, s), 5.29 (2H, s), 6.32–6.8 (2H, m), 7.0–7.56 (4H, m), 7.75 (1H, dd, J=2 Hz, 5 Hz),

Analysis Calcd. for C$_{20}$H$_{20}$N$_2$O$_2$: C: 74.98; H: 6.29; N: 8.74. Found: C: 74.98; H: 6.05; N: 8.71.

EXAMPLE 14

To a solution of sodium hydride (60% in mineral oil dispersion, 0.186 g) in 2-propynyl alcohol (8 ml) was added 8-(2-chlorobenzyloxy)-3-trimethylammoniomethyl-2-methylimidazo[1,2-a]pyridine iodide (2 g) and the mixture was heated at 90°–95° C. with stirring for 1 hour. After being cooled, the mixture was poured into ice-water and the resulting precipitate was collected by filtration and dissolved in methylene chloride. The solution was treated successively with silica gel (1 g) and activated charcoal and evaporated in vacuo. The crystalline residue was recrystallized from a mixture of methylene chloride and n-hexane to give 8-(2-chlorobenzyloxy)-3-(2-propynyloxymethyl)-2-methylimidazo[1,2-a]pyridine (0.9 g).

mp: 95° to 95.5° C.

IR (Nujol): 3280, 2120, 1575, 1545, 1295, 1070 cm$^{-1}$

NMR (CDCl$_3$, δ): ca. 2.4–2.7 (1H), 2.58 (3H, s), 4.13 (2H, d, J=2 Hz), 4.94 (2H, s), 5.47 (2H, s), 6.39–6.85 (2H, m), 7.10–7.50 (3H, m), 7.50–7.92 (2H, m)

Analysis Calcd. for C$_{19}$H$_{17}$ClN$_2$O$_2$: C: 66.96; H: 5.03; N: 8.22. Found: C: 67.13; H: 4.93; N: 8.12.

EXAMPLE 15

The following compounds were obtained according to similar manners to those of Examples 11, 13 and 14.

(1) 8-(1-Phenylethoxy)-3-(2-propynyloxymethyl)-2-methylimidazo[1,2-a]pyridine

IR (film/NaCl): 2100 cm$^{-1}$

NMR (CDCl$_3$, δ): 1.80 (3H, d, J=6 Hz), 2.40–2.60 (1H, m), 2.53 (3H, s), 4.05 (2H, d, J=2 Hz), 4.85 (2H, s), 5.52 (1H, q, J=6 Hz), 6.16–6.69 (2H, m), 7.11–7.56 (5H, m), 7.64 (1H, dd, J=1 Hz and 6 Hz).

(2) 8-(3-Chlorobenzyloxy)-3-(2-propynyloxymethyl)-2-methylimidazo[1,2-a]pyridine mp: 81° to 83° C. (recrystallized from petroleum ether)

IR (Nujol): 3130, 2095, 1570, 1540, 1285, 1055 cm$^{-1}$

NMR (CDCl$_3$, δ): 2.43–2.60 (1H, m), 4.52 (3H, s), 4.08 (2H, d, J=2 Hz), 4.88 (2H, s), 5.29 (2H, s), 6.32–6.80 (2H, m), 7.10–7.60 (4H, m), 7.75 (1H, dd, J=2 Hz and 7 Hz).

Analysis Calcd. for C$_{19}$H$_{17}$ClN$_2$O$_2$: C: 66.96; H: 5.03; N: 8.22. Found: C: 67.23; H: 4.88; N: 8.15.

(3) 8-(4-Chlorobenzyloxy)-3-(2-propynyloxymethyl)-2-methylimidazo[1,2-a]pyridine mp: 130° to 131° C. (recrystallized from a mixture of ethyl acetate and n-hexane)

IR (Nujol): 3240, 2100, 1530, 1490, 1360, 1275, 1256 cm$^{-1}$

NMR (CDCl$_3$, δ): 2.38–2.58 (1H, m), 2.52 (3H, s), 4.06 (2H, d, J=2 Hz), 4.86 (2H, s), 5.26 (2H, s), 6.26–6.73 (2H, m), 7.13–7.56 (4H, m), 7.76 (1H, dd, J=2 Hz and 7 Hz).

Analysis Calcd. for C$_{19}$H$_{17}$ClN$_2$O$_2$: C: 66.96; H: 5.03; N: 8.22. Found: C: 66.91; H: 4.95; N: 8.08.

(4) 8-(2-Bromobenzyloxy)-3-(2-propynyloxymethyl-2-methylimidazo[1,2-a]pyridine mp: 103° to 104° C. (recrystallized from a mixture of methylene chloride and diethyl ether)

NMR (CDCl$_3$, δ): 2.43–2.63 (1H, m), 2.52 (3H, s), 4.08 (2H, d, J=2 Hz), 4.88 (2H, s), 5.29 (2H, s), 6.33–6.81 (2H, m), 7.06–7.73 (4H, m), 7.75 (1H, dd, J=2 Hz and 7 Hz).

(5) 8-(2,6-Dichlorobenzyloxy)-3-(2-propynyloxymethyl)-2-methylimidazo[1,2-a]pyridine mp: 129° to 130° C. (recrystallized from a mixture of ethyl acetate and n-hexane)

IR (Nujol): 3290 cm$^{-1}$

NMR(CDCl$_3$, δ): 2.45–2.60 (1H, m), 2.46 (3H, s), 4.06 (2H, d, J=2 Hz), 4.86 (2H, s), 5.43 (2H, s), 6.60–6.85 (2H, m), 7.06–7.45 (3H, m), 7.80 (1H, dd, J=2 Hz and 3 Hz).

Analysis Calcd. for $C_{19}H_{16}Cl_2N_2O_2$: C: 60.81; H: 4.30; N: 7.47. Found: C: 61.31; H: 4.33; N: 7.48.

(6) 8-(3,4-Dichlorobenzyloxy)-3-(2-propynyloxymethyl)-2-methylimidazo[1,2-a]pyridine mp: 105° to 107° C. (recrystallized from a mixture of ethyl acetate and n-hexane)

IR (Nujol): 3260, 2110, 1280, 1160 cm$^{-1}$

NMR (CDCl$_3$, δ): 2.40–2.60 (1H, m), 2.46 (3H, s), 4.05 (2H, d, J=2 Hz), 4.83 (2H, s), 5.23 (2H, s), 6.26–6.80 (2H, m), 7.13–7.63 (3H, m), 7.75 (1H, dd, J=1 Hz and 7 Hz).

Analysis Calcd. for $C_{19}H_{16}Cl_2N_2O_2$: C: 60.81; H: 4.30; N: 7.47. Found: C: 61.26; H: 4.23; N: 7.55.

(7) 8-(2,4-Dichlorobenzyloxy)-3-(2-propynyloxymethyl)-2-methylimidazo[1,2-a]pyridine mp: 123° to 124° C. (recrystallized from a mixture of ethyl acetate and n-hexane)

IR (Nujol): 3250, 2110, 1280, 1060 cm$^{-1}$

NMR (CDCl$_3$, δ): 2.40–2.66 (1H, m), 2.50 (3H, s) 4.08 (2H, d, J=2 Hz), 4.90 (2H, s), 5.36 (2H, s), 6.30–6.83 (2H, m), 7.20 (1H, dd, J=2 Hz and 8 Hz), 7.40 (1H, d, J=2 Hz), 7.50 (1H, d, J=8 Hz), 7.80 (1H, dd, J=1 Hz and 7 Hz).

Analysis Calcd. for $C_{19}H_{16}Cl_2N_2O_2$: C: 60.81; H: 4.30; N: 7.47. Found: C: 61.29; H: 4.25; N: 7.41.

(8) 8-Benzyloxy-3-(2-propynyloxymethyl)imidazo[1,2-a]pyridine mp: 84° to 85° C. (recrystallized from diisopropyl ether)

IR (Nujol): 3170, 2100 cm$^{-1}$

NMR (CDCl$_3$, δ): 2.46 (1H, t, J=2 Hz), 4.13 (2H, d, J=2 Hz), 4.9 (2H, s), 5.33 (2H, s), 6.40–6.90 (2H, m), 7.23–7.60 (5H, m), 7.60 (1H, s), 7.83 (1H, dd, J=2 Hz and 7 Hz).

Analysis Calcd. for $C_{18}H_{16}N_2O_2$: C: 73.95; H: 5.52; N: 9.58. Found: C: 73.74; H: 5.30; N: 9.47.

(9) 8-Benzyloxy-3-(2-propynyloxymethyl)-2-phenylimidazo[1,2-a]pyridine

NMR (CDCl$_3$, δ): 2.40 (1H, t, J=1 Hz), 4.20 (2H, d, J=1 Hz), 4.96 (2H, s), 5.33 (2H, s), 6.40–6.80 (2H, m), 7.20–7.70 (8H, m), 7.76–7.96 (3H, m).

(10) 8-(2-Methylbenzylamino)-3-(2-propynyloxymethyl)-2-methylimidazo[1,2-a]pyridine hydrochloride mp: 159° to 161° C. (recrystallized from a mixture of ethanol and n-hexane)

NMR (DMSO-d$_6$, δ): 2.39 (3H, s), ca. 2.4–2.7 (3H, s), 3.50 (1H, t, J=2 Hz), 4.39 (2H, d, J=2 Hz), 4.50 (2H, broad d, J=5 Hz), 4.91 (2H, s), 6.73 (1H, d, J=8 Hz), 7.06–7.80 (6H, m), 7.91 (1H, d, J=6 Hz).

Analysis Calcd. for $C_{20}H_{22}ClN_3O$: C: 67.50; H: 6.23; N: 11.81. Found: C: 67.87; H: 6.43; N: 11.87.

(11) 8-(2-Chlorobenzylamino)-3-(2-propynyloxymethyl)-2-methylimidazo[1,2-a]pyridine hydrochloride mp: 169° C. (decomp.) (crystallized from a mixture of ethanol and diethyl ether)

NMR (DMSO-d$_6$, δ): 2.56 (3H, s), 3.52 (1H, t, J=2 Hz), 4.25 (2H, d, J=2 Hz), 4.85 (2H, broad s), 4.95 (2H, s), 6.73 (1H, d, J=8 Hz), 7.13–8.13 (7H, m)

Analysis Calcd. for $C_{19}H_{19}Cl_2N_3O$: C: 60.65; H: 5.09; N: 11.17. Found: C: 60.71; H: 5.39; N: 10.98.

(12) 8-Benzyloxy-3-allyloxymethyl-2-methylimidazo[1,2-a]pyridine mp: 70° to 71° C.

IR (Nujol): 1535, 1280, 1265, 1195, 1100, 1050, 1015 cm$^{-1}$

NMR (CDCl$_3$, δ): 2.50 (3H, s), 3.95 (2H, d, J=6 Hz), 4.76 (2H, s), 5.0–5.5 (2H, m), 5.33 (2H, s), 5.6–6.3 (1H, m), 6.36–6.79 (2H, m), 7.20–7.62 (5H, m), 7.75 (1H, dd, J=2 Hz and 6 Hz).

Analysis Calcd. for $C_{19}H_{20}N_2O_2$: C: 74.00; H: 6.54; N: 9.08. Found: C: 74.35; H: 6.48; N: 9.04.

(13) 8-Benzyloxy-3-(3-carboxy-2-propynyloxymethyl)-2-methylimidazo[1,2-a]pyridine mp: 151° C. (decomp.)

(14) 8-Benzyloxy-3-(3-ethoxycarbonyl-2-propynyloxymethyl)-2-methylimidazo[1,2-a]pyridine NMR (CDCl$_3$, δ): 1.33 (3H, t, J=5 Hz), 2.53 (3H, s), 4.20 (2H, s), 4.27 (2H, q, J=5 Hz), 4.90 (2H, s), 5.30 (2H, s), 6.50 (1H, dd, J=1 Hz and 5 Hz), 6.65 (1H, t, J=5 Hz), 7.26–7.60 (5H, m), 7.75 (1H, dd, J=d1 Hz and 5 Hz).

EXAMPLE 16

To a solution of 8-benzyloxy-3-(2-propynyloxymethyl)-2-methylimidazo[1,2-a]pyridine (1 g) in tetrahydrofuran (10 ml) was added dropwise 10% solution of n-butyllithium in n-hexane (2.09 ml) at −60° C. under a nitrogen atmosphere. After being stirred for 10 minutes the solution was treated with dry ice (1.4 g), allowed to warm to room temperature, and acidified with diluted acetic acid. The resulting precipitates were collected by filtration, washed with water, and recrystallized from methanol to give 8-benzyloxy-3-(3-carboxy-2-propynyloxymethyl)-2-methylimidazo[1,2-a]pyridine (0.67 g).

mp: 151° C. (decomp.)

NMR (DMSO-d$_6$, δ): 2.36 (3H, s),4.30 (2H, s), 4.85 (2H, s), 5.26 (2H, s), 5.93 (1H, broad s), 6.80–7.03 (2H, m), 7.26–7.63 (5H, m), 7.86–8.10 (1H, m).

Analysis Calcd. for $C_{20}H_{18}N_2O_4$: C: 65.04; H: 5.72; N: 7.36. Found: C: 65.07; H: 5.54; N: 7.35.

EXAMPLE 17

8-Benzyloxy-3-(3-ethoxycarbonyl-2-propynyloxymethyl)-2-methylimidazo[1,2-a]pyridine was obtained by reacting 8-benzyloxy-3-(2-propynyloxymethyl)-2-methylimidazo-[1,2-a]pyridine with ethyl chloroformate according to a similar manner to that of Example 16.

NMR (CDCl$_3$, δ): 1.33 (3H, t, J=5 Hz), 2.53 (3H, s), 4.20 (2H, s), 4.27 (2H, q, J=5 Hz), 4.90 (2H, s), 5.30 (2H, s), 6.50 (1H, dd, J=1 Hz and 5 Hz), 6.65 (1H, t, J=5 Hz), 7.26–7.60 (5H, m), 7.75 (1H, dd, J=1 Hz and 5 Hz).

What we claim is:

1. An imidazopyridine compound of the formula:

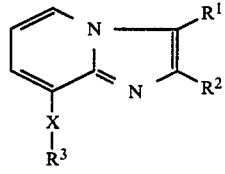

wherein
  $R^1$ is lower alkenyl, lower alkynyl, lower alkadienyl, lower alkenyloxy(lower)alkyl, lower alkynyloxy(lower)alkyl, carboxy(lower)alkynyloxy(lower)alkyl or lower alkoxycarbonyl(lower)alkynyloxy(lower)alkyl,
  $R^2$ is hydrogen, lower alkyl or aryl selected from the group consisting of phenyl, tolyl, xylyl, 1-naphthyl, 2-naphthyl, 1-anthryl and 2-anthryl, R³ is mono-(or di- or tri-)phenyl(lower)alkyl or naphthyl(lower)alkyl, each of which may have 1 to 3 suitable substituent(s) selected from the group consisting of lower alkyl and halogen;
mono-(or di- or tri-)phenyl(lower)alkenyl;
condensed bicyclic hydrocarbon group selected from the group consisting of naphthyl, 1,4-dihydronaphthyl, indenyl, benzene-condensed cyclo(lower)alkyl and perhydroindenyl;
lower alkyl substituted by cyclo(lower)alkyl;
or lower alkyl; and
X is O or NH,
or a pharmaceutically acceptable salt thereof.

2. A compound of claim 1, wherein:
R² is hydrogen, lower alkyl or phenyl,
R³ is phenyl(lower)alkyl or naphthyl(lower)alkyl, each of which may have 1 to 3 suitable substituent(s) selected from the group consisting of lower alkyl and halogen;
phenyl(lower)alkenyl;
benzene-condensed cyclo(lower)alkyl;
lower alkyl substituted by cyclo(lower)alkyl or lower alkyl.

3. A compound of claim 2, wherein
R³ is phenyl(lower)alkyl or naphthyl(lower)alkyl, each of which may have 1 to 3 suitable substituent(s) selected from a group consisting of lower alkyl and halogen.

4. A compound of claim 3, wherein
R¹ is allyl, 2-propynyl, 1,2-propadienyl, allyloxymethyl, 2-propynyloxymethyl, 3-carboxy-2-propynyloxymethyl or 3-ethoxycarbonyl-2-propynyloxymethyl,
R² is hydrogen, methyl or phenyl, and
R³ is benzyl which may have 1 or 2 suitable substituent(s) selected from a group consisting of methyl, ethyl, isopropyl, fluoro, chloro and bromo, 1-phenylethyl, 2-phenylethyl, 1-naphthylmethyl or 2-naphthylmethyl.

5. A compound of claim 4, which is selected from a group consisting of:
8-benzyloxy-3-allyl-2-methylimidazo[1,2-a]pyridine,
8-benzyloxy-3-(2-propynyl)-2-methylimidazo[1,2-a]pyridine,
[-(2-phenylethoxy)-3-(2-propynyl)-2-methylimidazo[1,2-a]-pyridine,
8-(2-methylbenzyloxy)-3-(2-propynyl)-2-methylimidazo[1,2-a]-pyridine,
8-(2-ethylbenzyloxy)-3-(2-propynyl)-2-methylimidazo[1,2-a]pyridine,
8-(2-isopropylbenzyloxy)-3-(2-propynyl)-2-methylimidazo[1,2-a]pyridine,
8-(2-chlorobenzyloxy)-3-(2-propynyl)-2-methylimidazo[1,2-a]-pyridine,
8-(3-chlorobenzyloxy)-3-(2-propynyl)-2-methylimidazo[1,2-a]-pyridine,
8-(4-chlorobenzyloxy)-3-(2-propynyl)-2-methylimidazo[1,2-a]-pyridine,
8-(2-bromobenzyloxy)-3-(2-propynyl)-2-methylimidazo[1,2-a]-pyridine,
8-(2-fluorobenzyloxy)-3-(2-propynyl)-2-methylimidazo-[1,2-a]-pyridine,
8-(2,6-dimethylbenzyloxy)-3-(2-propynyl)-2-methylimidazo-[1,2-a]-pyridine,
8-(2,6-dichlorobenzyloxy)-3-(2-propynyl)-2-methylimidazo-[1,2-a]pyridine,
8-(2-naphthylmethoxy)-3-(2-propynyl)-2-methylimidazo-[1,2-a]pyridine,
8-(1-naphthylmethoxy)-3-(2-propynyl)-2-methylimidazo-[1,2-a]pyridine,
8-(2-methylbenzylamino)-3-(2-propynyl)-2-methylimidazo-[1,2-a]pyridine,
8-(2-chlorobenzylamino)-3-(2-propynyl)-2-methylimidazo-[1,2-a]pyridine,
8-(2-methylbenzyloxy)-3-(1,2-propadienyl)-2-methylimidazo-[1,2-a]pyridine,
8-benzyloxy-3-(2-propynyloxymethyl)-2-methylimidazo[1,2-a]-pyridine hydrochloride,
8-benzyloxy-3-(2-propynyloxymethyl)-2-methylimidazo[1,2-a]-pyridine,
8-(1-phenylethoxy)-3-(2-propynyloxymethyl)-2-methylimidazo-[1,2-a]pyridine,
8-(2-methylbenzyloxy)-3-(2-propynyloxymethyl)-2-methylimidazo[1,2-a]pyridine,
8-(2-chlorobenzyloxy)-3-(2-propynyloxymethyl)-2-methylimidazo[1,2-a]pyridine,
8-(3-chlorobenzyloxy)-3-(2-propynyloxymethyl)-2-methylimidazo[1,2-a]pyridine,
8-(4-chlorobenzyloxy)-3-(2-propynyloxymethyl)-2-methylimidazo[1,2-a]pyridine,
8-(2-bromobenzyloxy)-3-(2-propynyloxymethyl)-2-methylimidazo[1,2-a]pyridine,
8-(2,6-dichlorobenzyloxy)-3-(2-propynyloxymethyl)-2-methylimidazo[1,2-a]pyridine,
8-(3,4-dichlorobenzyloxy)-3-(2-propynyloxymethyl)-2-methylimidazo[1,2-a]pyridine,
8-(2,4-dichlorobenzyloxy)-3-(2-propynyloxymethyl)-2-methylimidazo[1,2-a]pyridine,
8-benzyloxy-3-(2-propynyloxymethyl)imidazo[1,2-a]pyridine,
8-benzyloxy-3-(2-propynyloxymethyl)-2-phenylimidazo[1,2-a]-pyridine,
8-(2-methylbenzylamino)-3-(2-propynyloxymethyl)-2-methylimidazo[1,2-a]pyridine hydrochloride,
8-(2-chlorobenzylamino)-3-(2-propynyloxymethyl)-2-methylimidazo[1,2-a]pyridine hydrochloride,
8-benzyloxy-3-allyloxymethyl-2-methylimidazo[1,2-a]pyridine,
8-benzyloxy-3-(3-carboxy-2-propynyloxymethyl)-2-methylimidazo[1,2-a]pyridine, and
8-benzyloxy-3-(3-ethoxycarbonyl-2-propynyloxymethyl)-2-methylimidazo[1,2-a]pyridine.

6. A compound of claim 5, which is 8-(2-chlorobenzyloxy)-3-(2-propynyloxymethyl)-2-methylimidazo[1,2-a]pyridine.

7. A compound of claim 2, wherein
R¹ is lower alkynyl,
R² is lower alkyl,
R³ is phenyl(lower)alkenyl, 1,2,3,4-tetrahydronaphthyl, lower alkyl to substituted by cyclo(lower)alkyl or lower alkyl, and
X is O.

8. A compound of claim 7, wherein
R¹ is 2-propynyl,
R² is methyl, and
R³ is cinnamyl, 1,2,3,4-tetrahydro-1-naphthyl, cyclohexylmethyl or ethyl.

9. A compound of claim 8, which is selected from a group consisting of:
8-(cinnamyloxy)-3-(2-propynyl)-2-methylimidazo[1,2-a]-pyridine,
8-(1,2,3,4-tetrahydro-1-naphthyloxy)-3-(2-propynyl)-2-methylimidazo[1,2-a]pyridine,
8-cyclohexylmethoxy-3-(2-propynyl)-2-methylimidazo[1,2-a]pyridine, and 8-ethoxy-3-(2-propynyl)-2-methylimidazo[1,2-a]pyridine.

10. An antiulcerative pharmaceutical composition which comprises, as an active ingredient, an effective amount of a compound of claim 1 or a pharmaceutically acceptable salt thereof in admixture with pharmaceutically acceptable carriers.

11. A method for the treatment of ulcers which comprises administering an effective amount of a compound of claim 1 or a pharmaceutically acceptable salt thereof to a human or animal.

* * * * *